United States Patent
Spedden et al.

(10) Patent No.: US 9,446,164 B2
(45) Date of Patent: Sep. 20, 2016

(54) SURGICAL SUTURES INCORPORATED WITH STEM CELLS OR OTHER BIOACTIVE MATERIALS

(71) Applicant: BIOACTIVE SURGICAL, INC., Clarksville, MD (US)

(72) Inventors: Richard H. Spedden, Clarksville, MD (US); Laura J. Pingel, Ellicott City, MD (US); Lew C. Schon, Baltimore, MD (US)

(73) Assignee: BIOACTIVE SURGICAL, INC., Clarksville, MD (US)

( * ) Notice: Subject to any disclaimer, the term of this patent is extended or adjusted under 35 U.S.C. 154(b) by 0 days.

(21) Appl. No.: 14/518,535

(22) Filed: Oct. 20, 2014

(65) Prior Publication Data

US 2015/0051643 A1 Feb. 19, 2015

Related U.S. Application Data

(63) Continuation of application No. 12/489,557, filed on Jun. 23, 2009, now Pat. No. 8,876,864.

(60) Provisional application No. 61/075,122, filed on Jun. 24, 2008, provisional application No. 61/086,879, filed on Aug. 7, 2008, provisional application No. 61/165,055, filed on Mar. 31, 2009.

(51) Int. Cl.
*A61B 17/04* (2006.01)
*A61L 17/00* (2006.01)
(Continued)

(52) U.S. Cl.
CPC ........ *A61L 17/005* (2013.01); *A61B 17/06166* (2013.01); *A61L 17/06* (2013.01);
(Continued)

(58) Field of Classification Search
CPC .............. A61B 17/06166; A61B 2017/00884; A61B 2017/00893; A61B 2017/06185; A61L 17/06; A61L 2300/64
USPC ....... 606/222, 224, 228–231; 206/572, 63.3; 424/422–426
See application file for complete search history.

(56) References Cited

U.S. PATENT DOCUMENTS

| 4,027,676 A | 6/1977 | Mattei |
| 4,841,968 A | 6/1989 | Dunn et al. |

(Continued)

FOREIGN PATENT DOCUMENTS

| CN | 1596992 | 3/2005 |
| CN | 101163451 | 4/2008 |

(Continued)

OTHER PUBLICATIONS

Office Action for Japanese Appl. Ser. No. 2015-011428 dated Nov. 30, 2015.

(Continued)

*Primary Examiner* — Katherine M Shi
(74) *Attorney, Agent, or Firm* — Foley & Larder LLP; James F. Ewing

(57) ABSTRACT

Materials and methods for immobilizing bioactive molecules, stem and other precursor cells, and other agents of therapeutic value in surgical sutures and other tissue scaffold devices are described herein. Broadly drawn to the integration and incorporation of bioactive materials into suture constructs, tissue scaffolds and medical devices, the present invention has particular utility in the development of novel systems that enable medical personnel performing surgical and other medical procedures to utilize and subsequently reintroduce bioactive materials extracted from a patient (or their allogenic equivalents) to a wound or target surgical site.

10 Claims, 12 Drawing Sheets

(51) Int. Cl.
    *A61L 17/06*     (2006.01)
    *D06B 1/10*     (2006.01)
    *A61B 17/06*     (2006.01)
    *A61B 17/00*     (2006.01)

(52) U.S. Cl.
CPC .......... *D06B 1/10* (2013.01); *A61B 17/06114* (2013.01); *A61B 2017/00884* (2013.01); *A61B 2017/00893* (2013.01); *A61B 2017/06185* (2013.01); *A61L 2300/404* (2013.01); *A61L 2300/414* (2013.01); *A61L 2300/42* (2013.01); *A61L 2300/45* (2013.01); *A61L 2300/604* (2013.01); *A61L 2300/64* (2013.01)

(56) References Cited

U.S. PATENT DOCUMENTS

| | | |
|---|---|---|
| 5,800,829 A | 9/1998 | Dionne et al. |
| 5,919,473 A | 7/1999 | Elkhoury |
| 6,264,675 B1 | 7/2001 | Brotz |
| 7,353,810 B1 | 4/2008 | Blaschke |
| 7,357,810 B2 | 4/2008 | Koyfman et al. |
| 2004/0185250 A1 | 9/2004 | John |
| 2004/0199208 A1 | 10/2004 | Foerster |
| 2005/0004601 A1 | 1/2005 | Kong et al. |
| 2005/0149118 A1 | 7/2005 | Koyfman et al. |
| 2005/0149119 A1 | 7/2005 | Koyfman et al. |
| 2005/0182390 A1 | 8/2005 | Shanley |
| 2006/0047312 A1 | 3/2006 | Garcia Olmo et al. |
| 2007/0010856 A1 | 1/2007 | Cohen |
| 2007/0134305 A1 | 6/2007 | Zilberman |
| 2008/0128296 A1 | 6/2008 | Stopek et al. |

FOREIGN PATENT DOCUMENTS

| | | |
|---|---|---|
| JP | 2005-177499 | 7/2005 |
| JP | 2005-177500 | 7/2005 |
| JP | 2007-021189 | 2/2007 |
| JP | 2007-209748 | 8/2007 |
| WO | WO-2006/136244 | 12/2006 |
| WO | WO-2007/006639 | 1/2007 |
| WO | WO-2007/066339 | 6/2007 |
| WO | WO-2008/045338 | 4/2008 |

OTHER PUBLICATIONS

Extended European Search Report for EPO Appl. Ser. No. 09798479.3 dated Oct. 2, 2015.
Office Action for South Korean Appl. Ser. No. 10-2011-7001817 dated Aug. 4, 2015.
Notice of Reasons for Rejection for Japanese Application No. 2011-516506 dated Oct. 23, 2013, 7 pages.
Office Action for Canadian Patent Appl. Ser. No. 2765670 dated Jun. 1, 2015, 3 pages.
Office Action for Chinese Application No. 200980124331.3 dated Dec. 18, 2013, 11 pages.
Office Action for Chinese Application No. 200980124331.3 dated Apr. 7, 2013, 13 pages.
Office Action for Israeli Application No. 210183 dated Oct. 16, 2012, 2 pages.
Office Action for Israeli Application No. 210183 dated May 4, 2014, 1 page.
Office Action for Japanese Appl. Ser. No. 2011-516506 dated Sep. 25, 2014, 2 pages.
Supplementary Partial European Search Report for EPO Appl. Ser. No. 09798479.3 dated Jun. 9, 2015, 5 pages.
US Notice of Allowance for U.S. Appl. No. 12/489,557 dated Jun. 27, 2014, 11 pages.
US Office Action for U.S. Appl. No. 12/489,557 dated Dec. 21, 2011, 10 pages.
US Office Action for U.S. Appl. No. 12/489,557 dated Dec. 31, 2012, 9 pages.
US Office Action for U.S. Appl. No. 12/489,557 dated Mar. 29, 2012, 11 pages.
US Office Action for U.S. Appl. No. 12/489,557 dated Jun. 23, 2011, 14 pages.
Office Action for Canadian Appl. Ser. No. 2765670 dated Mar. 2, 2016.
Office Action for Chinese Appl. Ser. No. 201410400739.1 dated Feb. 1, 2016.

US 9,446,164 B2

SURGICAL SUTURES INCORPORATED WITH STEM CELLS OR OTHER BIOACTIVE MATERIALS

PRIORITY

The present application claims a priority benefit, under 35 U.S.C. 120, as a continuation application of U.S. patent application Ser. No. 12/489,557, filed Jun. 23, 2009, entitled "SURGICAL SUTURES INCORPORATED WITH STEM CELLS OR OTHER BIOACTIVE MATERIALS" and like that application, the instant application claims the benefit of U.S. Provisional Application Ser. No. 61/075,122 filed Jun. 24, 2008, 61/086879 filed Aug. 7, 2008, and 61/165,055 filed Mar. 31, 2009, which applications are hereby incorporated herein by reference in their entireties.

FIELD OF THE INVENTION

The present invention relates to the immobilization of bioactive materials, such as stem cells, other biological cells, bioactive molecules, particularly growth factors, and other materials of therapeutic value, in medical devices, particularly surgical sutures and tissue scaffolds, and the use of such sutures and scaffolds to afford controlled delivery of such materials to a patient, more particularly a target tissue site in need thereof. In addition to medical device constructs, precursors, kits and packaging systems therefore, the present invention provides methods of making and using such materials and includes in particular novel materials and methods that enable medical personnel in an operating room or other medical procedure environment to utilize bioactive materials extracted from a patient (e.g. autologous transplant materials) in a beneficial manner by subsequently reintroducing such transplant materials (or their allogenic equivalents) at a wound or target surgical site in the form of a therapeutic construct.

BACKGROUND OF THE INVENTION

Surgical sutures find common use in a broad range of medical procedures, often, but not exclusively, to hold skin, internal organs, blood vessels and all other tissues of the human body together after they have been severed by injury or surgery. In addition to serving as tissue fasteners, sutures and other elongate, thread-like medical devices can serve as a tissue scaffold or structural support for or during the growth of new tissue at a target tissue site, such as in tendon repair.

Sutures are available in a wide variety of forms, from monofilament to multi-filament to woven and braided filament construction, as a separate thread-like material or as a one-piece unit combined with a needle. They may be fabricated from a wide variety of biocompatible materials, ranging from non-absorbable materials such as cellulose (cotton, linen), protein-cellulose (silk), processed collagen (cat gut), nylon, polyester, polypropylene, aromatic polyamides ("aramid"), polytetraflourethylene, steel, copper, silver, aluminum, various alloys and the like, including many proprietary polymers and composites, to bioabsorbable (or biodegradable or bioerodible) synthetic materials, such as polymers and copolymers of glycolic and lactic acid.[1,2,3,4] Use of the latter—bioabsorbable materials—is often preferred as it avoids the need for additional surgical procedures (and the biological disruption associated therewith) to remove the suture.

[1] Middleton, John et al., "Synthetic Biodegradable Polymers as Medical Devices", Medical Plastics and Biomaterials Magazine (March, 1998).
[2] Shalaby, W et al., "Absorbable and biodegradable polymers", CRC Press, ISBN:0849314844 (2003).
[3] Kotwal V B et al., "Biodegradable polymers: Which, when and why?", Indian J Pharm Sci, 69 (5): 616-625 (2007).
[4] U.S. Pat. No. 6,838,493 to Williams et al. (2005).

In addition to being biocompatible, preferred suture materials should have good tensile strength, be compatible with a means of termination of the ends (such as tying or knotting), and be able to pass through the tissue during stitching with a minimum of friction or abrasion. Also, in cases where the suture passes through the skin or other barriers where fluid seepage could be an issue, a suture having reduced wicking properties, for example one having hydrophobic surface properties, is preferred. But apart from these desirable handling properties, it is also desirable that a suture, a material that is of necessity perceived by the immune system as "foreign", not induce an inflammatory response or foster infection. Even more preferable are sutures that actively prevent or inhibit inflammation and infection, that not only close wounds but actively contribute to full healing. For example, in addition to providing structural support to wounded tissue, it is also desirable for a tissue scaffold to interact with adhering and invading cells and effectively guide cellular growth and development of new tissue, for example by releasing bioactive molecules such growth factors and cytokines [see Tessmar, Joerg et al., "Matrices and Scaffolds for Protein Delivery in Tissue Engineering", Advanced Drug Delivery Reviews, 59 (4-5): 274-291 (May, 2007), incorporated by reference herein].

When selection of base materials and particular construction do not provide all the desired properties, it is known in the art to coat sutures with materials that achieve additional benefits, such as, but not limited to antimicrobial properties, tribologic properties, biocompatibility properties and properties to promote tissue growth or repair. Of particular interest is the inclusion in the suture coating of bioactive molecules, such as growth factors. For example, the use of sutures coated with a biodegradable matrix of various growth factor molecules has been shown to result in improved tissue regeneration at the application site [Dines, Joshua et al., "Biologics in Shoulder Surgery: Suture Augmentation and Coating to Enhance Tendon Repair", Techniques in Orthopaedics: Biologics in Shoulder Surgery, vol. 22(1):20-25, (March 2007)]. However, while selected growth factors introduced from synthetic production have proven to have benefit, they are costly to produce and may provide adverse reactions in the patient. In addition, the selected mix of components may not have the requisite range of therapeutic activity associated with endogenous tissues and fluids.

As for endogenous materials, graft materials such as bone marrow and adipose tissues, as well as particular components isolated therefrom, such as growth factors and stem or progenitor cells, also find utility in the context of sutures and tissue scaffolds. In contrast to synthetic materials, the mechanisms and modalities of which are often not fully understood, transplant of endogenous tissues, cells and molecules is known to result in a symbiotic, synergistic effect in the promotion of tissue growth. While transplant and graft materials may be obtained from an intended recipient (autografts) or a matched donor (allografts), the former has several distinct advantages such as inherent biocompatibility, ready access and availability and reduced cost.

In the context of graft materials, stem cells are of particular interest, possessing not only the ability to differentiate into a broad range of tissues but also the ability to trigger other biological processes, sending chemical signals that affect the differentiation of other cells, the recruitment of cells to a specific tissue region and/or the modulation of the immunoregulatory system (thereby facilitating rapid healing and possessing the potential additional benefits of reduced swelling and reduced scar tissue formation).

While the art is replete with examples of sutures provided with such therapeutic and/or bioactive materials (see, for example, U.S. Pat. No. 6,264,675 to Brotz et al. as well as U.S. Patent Publication 2006/0047312 to Olmo et al., 2008/0171972 to Stopek et al., all of which are incorporated by reference herein), the technology in this area is often focused on surface coatings, particularly those that afford the surface of the suture with either antimicrobial properties or a limited number of predetermined types of bioactive molecules, such as specific growth factors, which have been produced in a sterile production environment, often by recombinant techniques. However, such prefabricated synthetic coating systems often fail in the context of a biological environment, with the coating of interest either being substantially removed in the course of insertion (e.g., wiped or stripped through contact with neighboring tissue) or rapidly dispersed after introduction. Rarely is a sufficient concentration and density of bioactive material maintained at the target site over the requisite period of time needed for the suture (and the bioactive material associated therewith) to exert its beneficial effect. Though this effect may be countered by providing the suture surface with an overabundance of bioactive material, high local concentrations of bioactive material can result in deleterious, even toxic effects. Moreover, given the high cost of manufacture for certain bioactive materials, particularly natural and synthetic growth factors, this is not a cost effective solution.

In addition to the above-noted disadvantages, the prefabricated coating systems also cannot readily be adapted for use with transplant and graft materials, whether extracted from an intended recipient (autografts) or a matched donor (allografts). Presently available options for delivery of graft material generally involve either the direct injection of the material into an area of interest or the material is injected into to a bone graft or bone graft substitute prior to insertion; however, in either case, there is typically no system to immobilize the material in the area of interest.

Thus, the present invention addresses the need in the art for the controlled, long-term delivery of bioactive materials of interest, such as stem cells and/or therapeutic agents, to target tissue sites by integrating such materials within surgical fasteners and tissue scaffolds (generically referred to herein as "sutures"). The present invention not only provides for the capture and delivery of such bioactive molecules, but also provides unique configurations that facilitate the utilization of extracted tissues and fluid, whether from the intended recipient (i.e., autologous transplant materials) or a selected donor organism (i.e., allogenic, homologous or heterologous transplant materials), as well as materials that are synthetically produced or produced from cell cultures (recombinant transplant materials). In particular, embodiments of the medical device constructs, precursors, kits and packaging systems of the present invention have unique and valuable advantages over current art, including: (i) bioactive material extracted from the patient can be inserted into an interior core of a suture construct by medical personnel (as opposed to being remotely manufactured in a prefabricated state); (ii) stem and progenitor cells and other cells of interest can be immobilized at the point of interest, in proximity to other materials of value and within an exterior sheath afforded with the necessary permeability and biodegradability; and (iii) biodegradable particles containing bioactive materials can be incorporated in the interior core in a manner where the materials are immobilized without affecting the overall flexibility of the assembled suture.

SUMMARY OF THE INVENTION

Central to the instant invention is the provision of a surgical suture or elongate, linear or thread-like tissue scaffold in which the radial cross section comprises at least two concentric zones, which are differentiated in part by structure and by functionality, and wherein at least one interior zone comprises, in part, stem cells or other bioactive or therapeutic agents, and that said construct can be assembled prior to introduction into the intended host tissue. The two zones can share common elements or be of completely separate compositions. In the simplest construct, a hollow longitudinal structure, or sheath, of either porous or biodegradable nature (or a combination thereof), surrounds a longitudinal interior zone, or core, which comprises, in part, the stem cells or therapeutic materials. Alternatively, the sheath and core can comprise common structural elements and the differentiating factor can be the nature and density of the bioactive material present in each, for example a woven suture which forms a porous structure and wherein the core comprises an inner concentric zone in which the pores contain a higher concentration of stem cells and the sheath comprises an outer concentric zone in which the pores contain a barrier material, which tends to reduce the concentration of stem cells in that zone and thus reduce the migration of cells or other therapeutic materials out from the core into surrounding tissue for a period of time.

Accordingly, it is an object of the present invention to provide a surgical suture or elongate linear tissue scaffold having an exterior surface and an interior core, wherein: (i) the interior core is composed of one or more concentric inner zones, one or more of which contain a concentration of bioactive material, such as biological cells or therapeutic agents, dispersed there through; and (ii) the exterior surface is composed of one or more concentric outer zones or layers radially disposed about said interior core to control the migration of said bioactive material from said interior core to said exterior surface.

As described in greater detail below, the interior core retains the bioactive material of interest in a relatively immobilized state, using any suitable process, ranging from ionic or covalent binding to adsorption or absorption to simple physical capture, whether entrapment, entanglement or entrainment. The interior core may take the form of a porous, filamentous or woven structure or, alternatively, may take a more fluidic or viscous form, as a hydrogel, emulsion or foam, for example, or, alternatively, as rolled or coiled film layers. The interior core may further include or incorporate materials conducive to biological cell survival or growth, such as culture media, autologous or allogeneic fluids, and particularly media containing albumin.

The exterior surface acts like a protective sleeve, inhibiting the premature removal or migration of the bioactive material or contamination of the core with extraneous material or infectious materials during handling. The exterior surface may be disposed over a length of the interior core through relative movement (e.g. sliding, stretching) of one into or over the other, or, alternatively, by being wrapped about the radial periphery of the core, or, in a further embodiment, by being applied to the core in a liquid form that then transitions to a relatively solid state. The exterior sheath may be comprised of a film, extruded or coated onto the exterior of the suture core containing cells or bioactive materials as the interior core is extracted from the dispensing tube. Thermal plastics, solvent-based coatings and polymerizing coatings are of particular value in such a method.

The exterior sheath may also take the form of a porous, braided or woven sheath, a protective film-like layer, or a combination of the thereof. The exterior surface may further include or incorporate (a) a biodegradable component that forestalls the exodus of bioactive material until the suture is in place, in a target biological environment; (b) a particulate material that physically obstructs the pores or interstices of the underlying interior core to inhibit migration; or (c) a combination thereof. It may further include or incorporate components that afford beneficial properties, for example materials with a binding affinity for a biological tissue (e.g., tissue binding moieties such as fibrin, heparin, lectin, selectin, phage display products, aptamers or biocompatible adhesives such as cyanoacrylate); therapeutic agents such as antimicrobials, antibiotics, anticoagulants, and the like; anti-wicking hydrophobic materials; viscous, lubricating or adhesive materials; fatty acids and/or sialic acid moieties.

Although the invention is not limited to a particular bioactive material, the present invention is particularly suited to the transport and delivery of biological cells, such as stem, precursor and differentiated cells, as well as a wide range of graft and transplant materials, including autologous, homologous and heterologous transplant materials such as bone marrow and connective tissues It is a further object of the present invention to provide a surgical suture or tissue scaffold with a surface that includes a first layer of pliable appurtenances, for example, short, spike or fur-like fibers protruding from the surface, covered by a second layer of a biodegradable material that binds the protruding ends of the appurtenances to the exterior surface so as to initially afford the exterior surface with a relatively smooth profile, the biodegradable material being such that it degrades in a biological environment and releases said protruding ends so as to provide the exterior surface with relatively rough profile It is yet another object of the present invention to provide a suture precursor construct capable of being assembled into a suture or scaffold of the present invention, the precursor construct composed of: (i) a fixed length interior core capable of retaining a concentration of bioactive material, the interior core including a proximal portion and a distal portion; and (ii) a woven sheath in a compressed state disposed only about the proximal portion of the interior core, leaving the distal portion of the interior core exposed, wherein the woven sheath may be converted to an extended state wherein it covers both proximal and distal portions of said interior core to inhibit migration of said bioactive material out of said interior core, further wherein the woven sheath's compressed state length ranges from 5 to 90%, more preferably 10 to 70%, even more preferably 10 to 40% of its extended state length. As above, the interior core may take a number of alternate forms, from a plurality of filaments, woven, braided or separate, to a rolled or coiled layer of film, to a porous monofilament.

It is yet another object of the present invention to provide a surgical suturing kit composed of a suture precursor construct in a sterilizable package, optionally in combination with one or more additional suture threads, suture needles or other medical devices, the package having a plurality of discrete compartments including (i) a first compartment including a reservoir housing a distal portion of the suture precursor construct comprising an exposed section of interior core and an infusion port through which a bioactive material may be introduced, (ii) a second compartment housing the proximal portion of the suture precursor construct comprising one or more woven sheathing layers; and (iii) an optional third compartment comprising the one or more sutures, suture needles or other medical devices. The first compartment may further include an aspiration port for removing excess bioactive material from the reservoir. The second compartment preferably includes means to retain the one or more woven sheathing layers in a compressed state and may further include a second infusion port through which a second material may be introduced. The optional third compartment preferably houses a suture needle attached to the proximal end of said precursor construct. In use, the suture or suture precursor construct is drawn through the first and second compartments to facilitate the disposal of the one or more woven sheathing layers over the interior core to yield an assembled surgical suture or elongate tissue scaffold in which the one or more woven sheathing layers restricts the migration of bioactive material out of the interior core. The package may further include a transition seam between said first and second compartments, said transition seam including a constricted transformation point that facilitates the drawing of the exposed interior core into the exterior sheathing layer. The proximal ends of the interior core and the one or more woven sheathing layers are preferably joined to each other and to a shank end of a conventional suture needle while the distal ends of the interior core and the one or more woven sheathing layers may each be afforded with coordinating stop components that mate and interlock when the sheathing layer is fully extended over an exposed interior core. In one embodiment, the sheathing layer distal stop may be integral with the transition seam, such that the stop components mate, interlock and inhibit subsequent relative motion of the two distal ends when the interior core is fully drawn across said transition seam and into said second compartment.

In another embodiment of coordinating stop components, either the distal end of a sheathing layer or the distal end of a core can have a distal stop component of a design which can be crimped or otherwise engage the unadorned distal end of the core or sheath, respectively.

In the preferred embodiment of the above-described kit, the first and second compartments are hydraulically isolated. In alternate embodiments, they are in hydraulic communication, optionally including a constricted transformation point disposed between the second compartment and the proximal end of the suture construct in the package.

In an alternate embodiment, the a surgical suturing kit may include a surgical suture precursor construct in a sterilizable package in combination with one or more sutures, suture needles or other medical devices, the package having plurality of discrete compartments including (i) a first compartment including a reservoir and an infusion port through which a bioactive material may be introduced, wherein the reservoir retains in a deformed state a distal portion of a precursor construct having an exterior surface and an interior core and comprised of a matrix of interwoven filaments or a porous monofilament, such that the interstices between interwoven filaments or the pores of the monofilament are of a first size and shape sufficient to permit the migration of bioactive material introduced into said reservoir, across the exterior surface, and into the interior core; (ii) a transforming port through which a proximal portion of the precursor passes to form a surgical suture, wherein the port is of a design which induces the interstices or pores to take a second size and shape sufficient to restrict the migration of the bioactive material from the interior core across the exterior surface; and (iii) an optional second compartment abutting the transforming port comprising the one or more sutures, suture needles or other medical devices.

In yet a further alternate embodiment, the surgical suturing kit may include a surgical suture precursor construct in a sterilizable package in combination with one or more sutures, suture needles or other medical devices, the package having plurality of discrete compartments through which the precursor construct may be serially drawn and in which the precursor construct may be exposed to different materials for incorporation into the assembled suture as a series of concentric layers. The surgical suture precursor may optionally comprise a porous construct and the plurality of discrete compartments may optionally include: (i) a first compartment comprising a reservoir and an infusion port through which a bioactive material may be introduced such that the material interacts with the pores of the suture precursor; and (ii) a second compartment containing a barrier material or a means for introducing a barrier material into contact with the precursor such that a precursor drawn from the first compartment through the second compartment results in the barrier material overlaying the bioactive material in the resulting suture construct.

In addition to medical device constructs, precursors, kits and packaging systems therefore, it is yet a further object of the present invention to provide a method of making a surgical suture (or an elongate, linear and/or thread-like tissue scaffold) having an exterior surface and interior core comprised of a matrix of interwoven filaments or a porous monofilament, wherein a concentration of a bioactive material such as biological cells or therapeutic agents is dispersed throughout said interior core, the method including the steps of: (a) compressing or otherwise manipulating the matrix along or around a longitudinal axis so as to deform the interstices between interwoven filaments or the pores of the monofilament to a first size and shape sufficient to permit the migration of the bioactive material from a surrounding media, across the exterior surface, and into the interior core; and (b) manipulating the bioactive material-containing matrix along or around the longitudinal axis so as to shrink the interstices or pores to a second size and shape sufficient to restrict the migration of the bioactive material from the interior core across the exterior surface. In the context of this method, the exterior surface may optionally comprise a porous sheath, such that the manipulation of step (b) involves deforming the sheath along or around the longitudinal axis so as to reduce at least one dimension of a pore opening in the sheathing layer and thereby reduce the size of particles which can potentially pass through said pore opening. Alternatively, the manipulation of step (b) may involve deforming the sheath along or around the longitudinal axis so as to constrict the sheathing layer about the core contained therein in a manner that impairs migration of the bioactive material within the core. In a preferred embodiment, the bioactive material includes particles of a size that are capable of traversing the pores of the first size and shape but incapable of traversing the pores of the second size and shape.

It is yet a further object of the present invention to provide a method of making a surgical suture or tissue scaffold having an exterior surface of woven or film construct and an interior core comprised of multiple filaments or a porous monofilament, wherein a concentration of a bioactive material such as biological cells and therapeutic agents is dispersed throughout the interior core, the method comprising the steps of: (a) providing an exposed section of the interior core without the surrounding sheath; (b) contacting the exposed section with a media containing the bioactive material, such that the bioactive material is entrained in among the core fibers or in the pores of said core; and (b) manipulating the core or the sheath to cause the core to be surrounded by the sheath with bioactive material present in the core.

It is yet a further object of the present invention to provide a method for applying a target agent to a portion of a medical device and subsequently coating or covering the portion with additional agents or materials to yield a coated target agent-containing medical device, the method including the following steps:

providing a sterile package comprising a reservoir housing a medical device or portion thereof, at least one infusion port configured to permit the sterile introduction of at least one target agent into the reservoir, and at least one aspiration port configured to permit the sterile expulsion of at least one target agent, wherein the infusion port and aspiration port may optionally be a common port;

optionally introducing a binding agent that facilitates the binding of a target agent to the medical device into the reservoir via the at least one infusion port and optionally expelling any excess binding agent from the reservoir via the at least one aspiration port;

introducing a target agent into the reservoir through the at least one infusion port and permitting the medical device to bind, absorb, adsorb, or otherwise immobilize said target agent;

expelling residual target agent from the reservoir through the at least one aspiration port;

optionally introducing a flushing material into the reservoir to facilitate dilution and removal of excess target agent and subsequently expelling the flushing material from the reservoir through the at least one aspiration port; and introducing one or more additional target agents or coating molecules into the reservoir via the at least one infusion port and permitting said medical device to bind, absorb, adsorb, or otherwise immobilize the additional target agents or coating materials.

It is yet a further object of the present invention to provide a method of serially exposing a medical device to multiple target agents or materials, the method including the following steps:

providing a sterile package comprising two or more discrete compartments or zones, a first of which houses a medical device or portion thereof and includes at least one infusion port configured to permit the sterile introduction of at least one target agent into the compartment;

introducing a target agent into the first compartment through the at least one infusion port and permitting the medical device to bind, absorb, adsorb, or otherwise immobilize said target agent; and drawing the target agent-containing medical device into a second compartment and exposing the device to one or more additional target agents or coating molecules.

It will be understood by those skilled in the art that one or more aspects of this invention can meet certain objectives, while one or more other aspects can meet certain other objectives. Each objective may not apply equally, in all its respects, to every aspect of this invention. As such, the preceding and subsequently presented objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF THE DRAWINGS

Various aspects and applications of the present invention will become apparent to the skilled artisan upon consideration of the brief description of the figures and the detailed description of the present invention and its preferred embodiments that follows:

FIG. 3A depicts the material in a compressed "open" state. FIG. 3B is a representation of the pores of the material of FIG. 3A, having an "open" geometry that may be permeated or traversed by a material of interest (35). FIG. 3C depicts the material in an extended "closed" state. FIG. 3D is a representation of the pores of the material of FIG. 3C, having constricted impenetrable pores.

FIG. 7 depicts lateral views of an illustrative example of a surgical suture (70) of the present invention in pre-assembled (FIG. 7A) and assembled states (FIG. 7B).

DETAILED DESCRIPTION OF THE PRESENT INVENTION AND PREFERRED EMBODIMENTS

Figure 1:
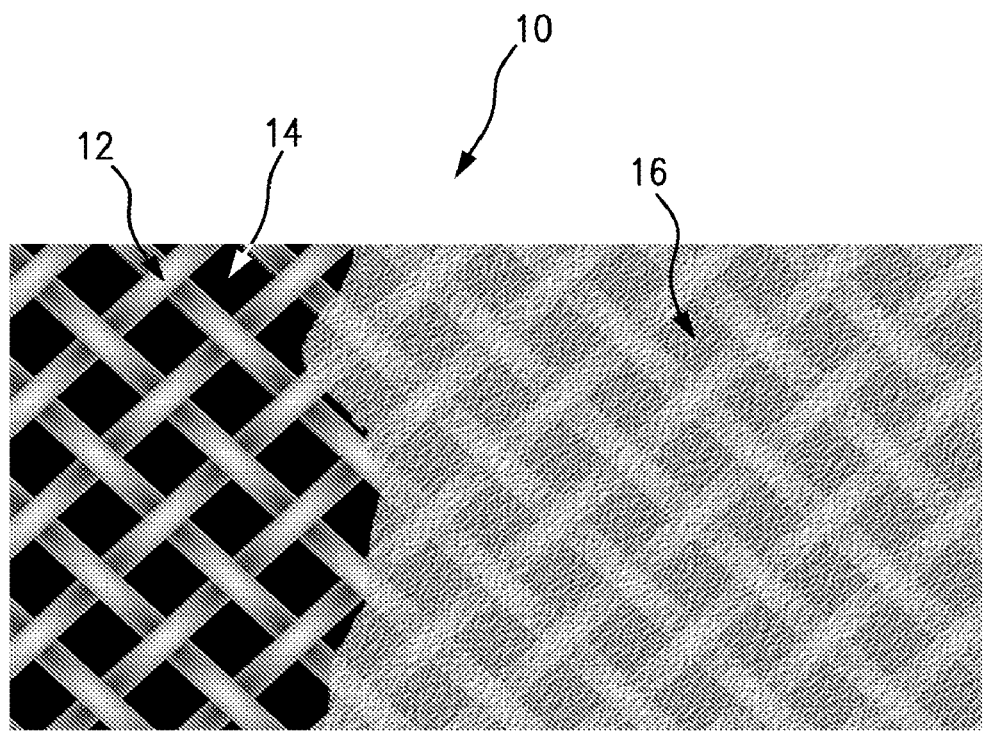
FIG. 1 depicts an illustrative example of a woven material (10) suitable for use in the fabrication of surgical sutures of the present invention, in which interwoven filaments (12) define corresponding interstitial pores or interstices (14). The material is depicted with (right side) and without (left side) a corresponding non-polar film (16) disposed thereover. The film acts as a barrier, obstructing the interstices of the woven material.
Figure 2:
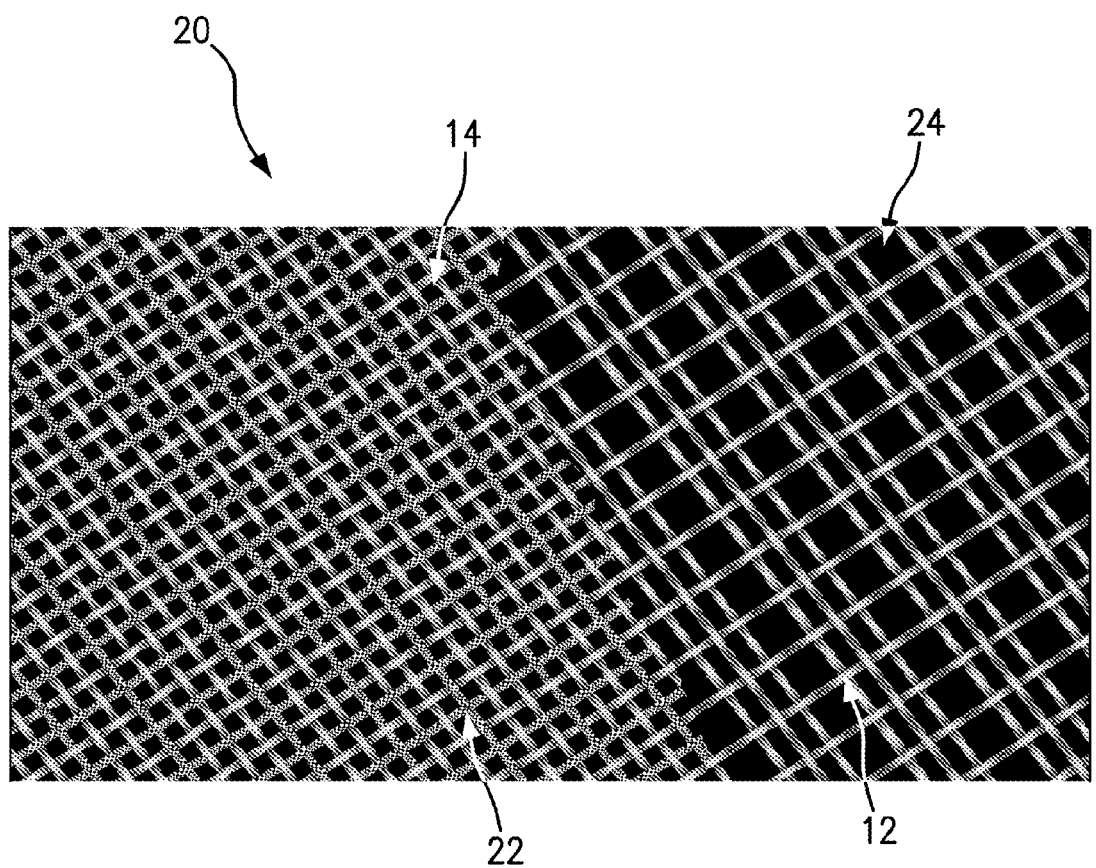
FIG. 2 depicts an illustrative example of a woven material (20) suitable for use in the fabrication of surgical sutures of the present invention, formed from a weave of both conventional (12) and rapidly degradable (22) filaments. As in FIG. 1, the interwoven filaments define a plurality of pores or interstices (14, 24). The left side of the figure depicts the pre-woven material with the rapidly degradable filaments intact. The right side of the figure depicts the woven material after the rapidly degradable filaments have dispersed (degraded, dissolved, or the like). Degradation of a portion of the filaments results in a loosening of the weave and enlargement of the corresponding interstices (24).
Figure 3:
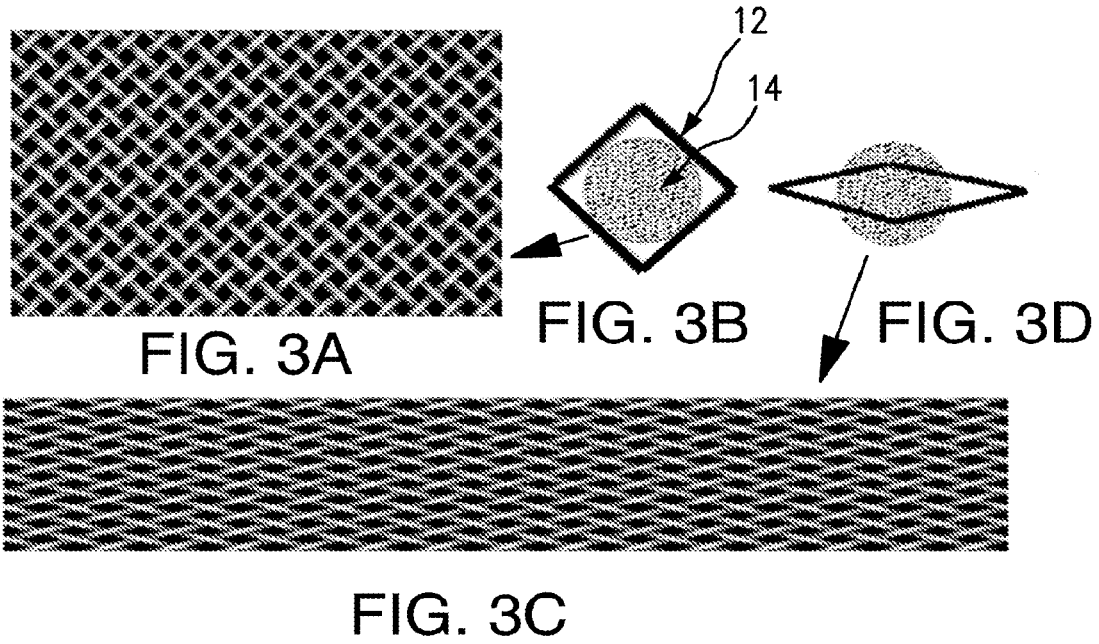
FIG. 3 depicts an illustrative example of a woven material (30) suitable for use in the fabrication of surgical sutures of the present invention, formed from plurality of interwoven filaments (12) that define a plurality of pores or interstices (14).
Figure 4:
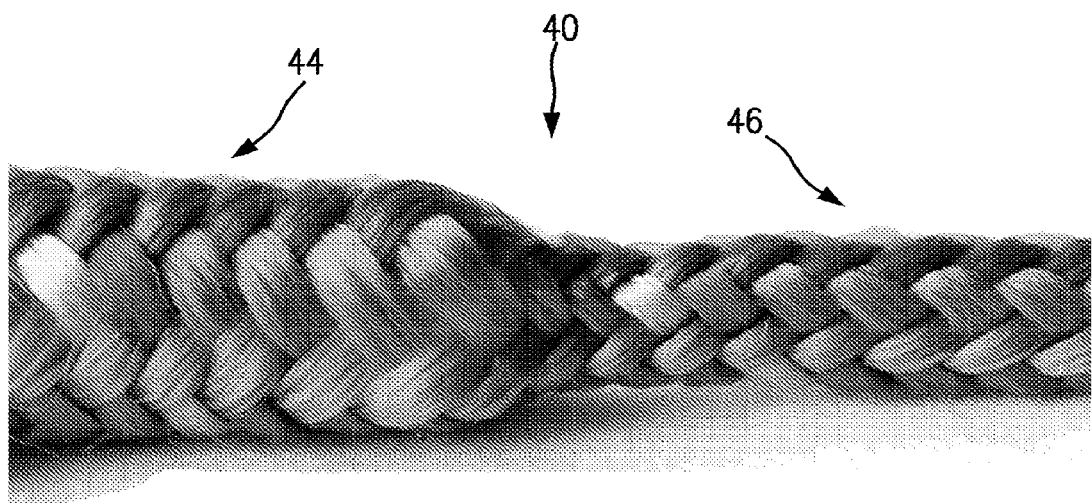
FIG. 4 is a photograph of an illustrative example of a woven sheath (40) suitable for use in the fabrication of surgical sutures of the present invention, the sheath depicted in transition from compressed state (left side, 44) to extended state (right side, 46).

The present invention relates to sutures and suture precursor constructs composed of a bioactive material-bearing suture core having a protective exterior sheath or film disposed thereover to inhibit premature removal or migration of the bioactive material. Described in greater detail herein are suitable sheath structures, suitable suture core structures, suitable means of immobilizing biological cells and therapeutic agents in said structures, therapeutic combinations of agents in said structures, methods for delivering agents to the structures and assembling structures, methods of use and kits and packaging associated with the elements of the present invention.

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the present invention, the following definitions apply:

A. Elements of the Present Invention:

As used herein and in the appended claims, the singular forms "a", "an" and "the" include plural reference unless the context clearly dictates otherwise. Thus, for example, reference to a "molecule" is a reference to one or more molecules and equivalents thereof known to those skilled in the art, and so forth.

In the context of the instant invention, the term "medical device" encompasses both devices intended for limited or temporary introduction (for example, bioerodible sutures or tissue scaffolds) as well as devices intended for long term or permanent insertion (for example, artificial ligaments or tendons). As used herein and in the appended claims, the term "medical device" refers to any apparatus, appliance, instrument, implement, material, machine, contrivance, implant, in vitro reagent, or other similar or related article including a component party or accessory which is intended for the diagnosis, prevention, monitoring, treatment or alleviation of disease, injury or handicap. It further encompasses any article intended to affect the structure or function of the body of humans or other animals, and which does not achieve its principal intended action in or on the body exclusively by pharmacological, immunological or metabolic means, but which may be assisted in its function by such means. Illustrative examples of medical devices contemplated by the present invention include, but are not limited to, needles, catheters (e.g., intravenous, urinary, and vascular catheters), stents, shunts (e.g., hydrocephalus shunts, dialysis grafts), tubes (e.g., myringotomy tubes, tympanostomy tubes), implants (e.g., breast implants, intraocular lens), prosthetics, and artificial organs, as well as cables, leads, wires, and electrodes associated therewith (e.g., leads for pace makers and implantable defibrillators, bipolar and monopolar RF electrodes, vascular guidewires). Also contemplated are devices such as wound dressings, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, ligament or tendon implant devices, intraluminal devices, vascular supports, and other body contacting devices that may benefit from incorporation with therapeutic materials such as therapeutic agents, bioactive molecules, and biological cells or tissues.

As used herein, the term "suture" refers to an elongate, generally tubular and thread-like medical device provided with a proximal end, a distal end and a longitudinal axis, where the length along the longitudinal axis is equal to or greater than the twice the length on any other axis, and where the device is flexible along the longitudinal axis. Typically, sutures are used to join tissue or medical prosthesis; however in the context of the present invention, sutures can also be of value in the immobilization and delivery of therapeutic materials to a tissue site or as a scaffold for tissue growth.

The term "structural properties" in the context of a suture generally refers to those properties that permit the device to withstand tensile forces in the longitudinal, circumferential or radial directions without premature failure or a level of yield that would prevent the device from functioning in its intended manner over the anticipated functional life of the device.

The term "porous" in the context of the present invention relates to voids or openings of functionally relevant size in the matrix of materials in the sheath or core of the present invention. In the context of openings in or passageways through or out of the sheath or the core, the functionally relevant size is the size that permits or inhibits passage of cells, therapeutic materials or other materials of the construct that might otherwise have mobility. In the case of stem cells and other biological cells, the functionally relevant size to permit passage of single cells is a size greater than the cell size, which is typically in the 5 to 50 µm range. Though since in many situations, the goal is to inhibit flow and total prevention of flow is not required, a much larger diameter opening could provide the desired result, particularly in the case where any interstitial fluid (or cell carrier media) has a viscosity sufficient to retard flow, the flow path is relatively long or convoluted, or where other materials present in the fluid which is of a size or density to impede flow. In most cases, particularly with a woven matrix as is common in sutures and in the preferred embodiment of a sheath of the present invention, the openings in a porous media, such as a sheath, are not round, and in many cases the geometry varies as to the type of stress that the media is put under; in such cases, the relevant dimension will usually be the minimum dimension across the opening.

Relevant porosity, in the case of bulk media, such as in the core of a suture which comprises biological cells are those voids which are of a size to include therapeutic materials in a total quantity in the media to have therapeutic effect, or those voids of a size necessary to allow inclusion of biological cells in the media. In the case of a suture core, relevant voids can include the space between fibers in a multifilament core, the space between the core and the sheath, the space between particles is a particulate-bearing core, or voids in the actual bulk material in the core (for example a sponge-like material). Studies have indicated that there are benefits to stem cell proliferation and differentiation with pore sizes in the 100 to 500 µm range, though pore sizes outside of that range also are of value in the present invention.[5]

[5] Mygind T, et al., "Mesenchymal stem cell ingrowth and differentiation on coralline hydroxyapatite scaffolds", Biomaterials, 28 (6): 1036-1047 (February 2007).

Medical devices, particularly surgical sutures, can be fabricated from a wide range of materials. Of particular interest in certain aspects of the present invention are materials which are biodegradable and biocompatible. Biodegradable polymers can include but are not limited to the polyester family, such as polyglycolides and polylactides, the polyorthoesters family, the polyanhydrides family, the polyphosphazenes family and polyhydroxyalkanoates. More specific examples of biocompatible polymers include: polyesters of [alpha]-hydroxycarboxylic acids, such as poly(L-lactide) (PLLA) and polyglycolide (PGA); poly-p-dioxanone (PDO); polycaprolactone (PCL); polyvinyl alcohol (PVA); polyethylene oxide (PEO); polymers disclosed in U.S. Pat. Nos. 6,333,029 and 6,355,699; and any other bioresorbable and biocompatible polymer, co-polymer or mixture of polymers or co-polymers that are utilized in the construction of medical implant devices.

Additionally, natural materials are in common use in medical devices, for example: collagen and silk. Some of these biocompatible materials can be conjugated with bioactive molecules, such as growth factors, using technologies including those listed in patents referenced herein. Said biodegradable materials can also include materials which may or may not be suited to conjugation with bioactive molecules. Certain aspects of the present invention permit incorporation of bioactive molecules into the construct of a medical or surgical device construct without necessitating conjugation, also chemical bonding, with the device material and as a consequence, any biodegradable and/or biocompatible material which has value as a part of a medical device, for example a surgical suture construct, is of value in the present invention. In addition, as new biocompatible, bioresorbable materials are developed, it is expected that at least some of them will be useful materials in the context of the present invention. It should be understood that the above materials are identified by way of example only, and the present invention is not limited to any particular material unless expressly called for in the claims.

Bone marrow for clinical use is typically obtained as an aspirate extracted from a target patient's bone using a syringe-type device. Often the hip bone is used as a source due to its large size and proximity to the surface of the body. In some applications, the bone marrow is used without modification, but in many cases some form of separation technology, such as centrifugation, is used to concentrate the desired fraction of the bone marrow. Bioactive molecules, including cytokines such as growth factors, are often the target of this separation process. Stem cells, progenitor cells or other cells can also be desired targets. Cells and molecules of interest are also typically obtained from adipose, also fat, tissue, as well as from various fluids in the body. Any tissue of the body has potential, muscle and nerve tissue and tissues associated with the reproductive process are also of particular interest. Material extracted from the patient has several advantages over other sources, such as: inherent biocompatibility, potential for lower cost, providing a broader spectrum of useful compounds which might have synergistic effects. In current surgical practice, bone marrow derivatives are typically reintroduced into the body by injection by syringe into an area of desired activity. Often a porous retention media such as a collagen sponge is used to retain the material in the area.

The term "cell" or "biological cell" refers to any cell capable of performing useful biological functions in a living organism, particularly replication to form a tissue structure. Biological cells may include cells from the intended host organism or those from a donor organism. Biological cells can include cells from recombinant or genetic engineering techniques. The term as used herein includes stem cells, progenitor cells and fully differentiated cells, include one or more of the following: chondrocytes; fibrochondrocytes; osteocytes; osteoblasts; osteoclasts; synoviocytes; bone marrow cells; mesenchymal cells; stromal cells; stem cells; embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value, it is anticipated that at least some of these cells will have use in the concepts of the present disclosure, and such cells should be included within the meaning of "cell" and "cells" unless expressly limited otherwise.

The term "stem cell" represents a generic group of undifferentiated cells that possess the capacity for self-renewal while retaining varying potentials to form differentiated cells and tissues. Stem cells can be totipotent, pluripotent or multipotent. Derivative stem cells that have lost the ability to differentiate also occur and are termed 'nullipotent' stem cells. A totipotent stem cell is a cell that has the ability to form all the cells and tissues that are found in an intact organism, including the extra-embryonic tissues (i.e. the placenta). Totipotent cells comprise the very early embryo (8 cells) and have the ability to form an intact organism. A pluripotent stem cell is a cell that has the ability to form all tissues found in an intact organism although the pluripotent stem cell cannot form an intact organism. A multipotent cell has a restricted ability to form differentiated cells and tissues. Typically adult stem cells are multipotent stem cells and are the precursor stem cells or lineage restricted stem cells that have the ability to form some cells or tissues and replenish senescing or damaged cells/tissues. Further information may be found in WO 08/007082, the contents of which are incorporated by reference herein.

The term "progenitor cell" refers to unipotent or multipotent cells, which comprise the stage of cell differentiation between stem cells and fully differentiated cells.

The term "bioactive molecules" refers to any molecule which has the capacity to interact with a living tissue or system in such a way as to exhibit or induce a biological activity in an organism, tissue, organ or cell, either in vivo, in vitro or ex vivo. The term "bioactive molecule" extends to precursor forms thereof. Precursor proteins, for example BMP precursors, are typically inactive until they undergo endoproteolytic cleavage; however, in that this is a process that naturally occurs in the body, the present invention extends to precursor proteins that participate in useful biological processes in the body.

Of particular interest in the context of the present invention are bioactive peptides that trigger or regulate biological functions. Illustrative examples of bioactive molecules suitable for use in the context of the present invention include, but are not limited to, are growth factor proteins, such as TGFβ, BMP-2, FGF and PDGF.

As used herein and in the appended claims, the term "growth factors" refers to the broad class of bioactive polypeptides that control or regulate a variety of endogenous biological and cellular processes, such as cell-cycle progression, cell differentiation, reproductive function, development, motility, adhesion, neuronal growth, bone morphogenesis, wound healing, immune surveillance and cell apoptosis. Growth factors typically operate by binding to specific receptor sites on the surface of target cells. Growth factors include, but are not limited to, cytokines, chemokines, polypeptide hormones and the receptor-binding antagonists thereof. Examples of well known growth factors include but are not limited to:

Bone Morphogenic Protein (BMP);
Transforming growth factor beta (TGF-β);
Interleukin-17;
Transforming growth factor alpha (TGF-α);
Cartilage oligomeric matrix protein (COMP);
Cell Density Signaling Factor (CDS);
Connective tissue growth factor (CTGF);
Epidermal growth factor (EGF);
Erythropoietin (EPO);
Fibroblast growth factor (FGF);
Glial Derived Neurotrophic Factors (GDNF);
Granulocyte-colony stimulating factor (G-CSF);
Granulocyte-macrophage colony stimulating factor (GM-CSF);
Growth differentiation factor (GDF);
Myostatin (GDF-8);
Hepatocyte growth factor (HGF];
Insulin-like growth factor (IGF);
Macrophage inhibitory cytokine-1 (MIC-1);
Placenta growth factor (PIGF);
Platelet-derived growth factor (PDGF);
Thrombocyte concentrate (PRP);
Thrombopoietin (TPO);
Vascular endothelial growth factor (VEGF);
Activin and Inhibin;
Coagulogen;
Follitropin;
Gonadotropin and Lutropin;
Mullerian Inhibiting Substance (MIS) also called: Anti-Müllerian hormone (AMH) Müllerian inhibiting factor (MIF) and Mullerian inhibiting hormone (MIH);
Nodal and Lefty; and
Noggin Molecules which regulate, induce or participate in useful biological processes in the body, including those listed above, are often categorized or classified according to their particular structure or function. For example, immunoregulatory proteins secreted by cells of the immune system, such as interleukin and interferon, are often referred to as cytokines. Other categories of regulatory molecules include, but are not limited to:

- morphogens (e.g., molecules that regulate or control the formation and differentiation of tissues and organs);
- chemokines (e.g., any of a group of cytokines produced by various cells, as at sites of inflammation, that stimulate chemotaxis in white blood cells such as neutrophils and T cells);
- hormones (e.g., a product of living cells that circulates in body fluids such as blood and produces a specific, often stimulatory effect on the activity of cells, usually remote from its point of origin);
- receptors (e.g., a molecule present on a cell surface or in the cell interior that has an affinity for a specific chemical entity, including both endogenous substances such as hormones and ligands as well as foreign materials, such as viral particles, that serves as an intermediary between the stimulating agent and the downstream physiological or pharmacological response thereto;
- receptor-binding agonists (e.g., a chemical substance capable of combining with a specific receptor on a cell and initiating the same reaction or activity typically produced by the endogenous binding substance (such as a hormone); and
- receptor-binding antagonists (e.g., a chemical substance that reduces the physiological activity of another chemical substance (such as a hormone) by combining with and blocking one or more receptors associated therewith).

However, since the study of the function of the various regulating moieties in the body is still an emerging science, the categorization thereof is also evolving. Accordingly, the present invention is not limited to any one particular class or category of regulating or stimulating molecules.

As used herein and in the appended claims, the term "growth factors" also refers to precursor forms of growth factors, which are typically inactive until they undergo endoproteolytic cleavage, as well as synthesized and recombinant forms which provide part or all of the same or similar functions as the naturally occurring growth factors. Accordingly, the present invention encompasses precursors, analogues, and functional equivalents of growth factors, provided the resulting molecules retain some or all of the function of regulating useful biological processes in the body, typically by binding to specific receptor sites on the surface of target cells associated with the wild-type or endogenous moiety.

The term "therapeutic agents" as used herein refers to any molecule, compound or composition having therapeutic potential, more particularly pharmaceutical activity. Examples of particularly useful therapeutic and/or pharmaceutical activities include but are not limited to anti-coagulation activity, anti-adhesive activity, anti-microbial activity, anti-proliferative activity, and biomimetic activity.

The term "antimicrobial" refers to any molecule that has the capacity to limit or interfere with the biological function of a bacterial, fungal or viral pathogen or a toxin. Antimicrobial is intended to also encompass antibacterial, antibiotics, antiseptics, disinfectants and combinations thereof.

In the context of the present invention, the term "biomimetic" refers to a material which exhibits surface properties, including but not limited to molecular structures such as amino acid and carbohydrate sequences, which provide the surface with characteristics, and in particular molecular binding or biological recognition features, which are in common with or provide functional analogues with biological features of biological materials such as tissue, and in particular cells, which the surface is intended to represent. The term biomimetic in the context of the present invention does not require that the surface duplicate all functions or binding modalities of the biological material being mimicked. Examples of preferred structures to be mimicked include pathogen binding proteins and immune recognition sequences (e.g., glycan signatures). Whether a particle moiety possesses the requisite biomimetic activity may be routinely assayed using conventional techniques known to those skilled in the art. For example, one may utilize well known immunoassay techniques, such as ELISA, to assay the binding activity of a proposed biomimic as compared to endogenous host tissue. Likewise, one may utilize conventional immune response assays, such the multiplexed chemokine and cytokine assays available through Meso Scale Discovery (MSD) (Gaithersburg, Md.), to assess the risk and assay immunogenic potential of a proposed biomimic as compared to native tissue.

The term "therapeutic materials" refers to any composition that comprises any of the following: therapeutic agents, bioactive molecules, stem cells, progenitor cells or biological cells. The term "bioactive solution" refers to a liquid composition that comprises, in part, bioactive materials.

As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents.

As used herein, the term "bone" refers to the rigid organs that form part of the endoskeleton of vertebrates and function to move, support, and protect the various organs of the body, produce red and white blood cells and store minerals. One of the types of tissues that make up bone is the mineralized osseous tissue, also called bone tissue, which gives it rigidity and honeycomb-like three-dimensional internal structure. Other types of tissue found in bones include marrow, endosteum, and periosteum, nerves, blood vessels and cartilage.

Cartilage is a type of dense connective tissue composed of collagen fibers and/or elastin fibers that can supply smooth surfaces for the movement of articulating bones. Cartilage is found in many places in the body including the joints, the rib cage, the ear, the nose, the bronchial tubes and the intervertebral discs. There are three main types of cartilage: elastic, hyaline, and fibrocartilage.

Accordingly, the term "tissue" as used herein broadly encompasses all biological components including, but not limited to, skin, muscle, nerves, blood, bone, cartilage, tendons, ligaments, and organs composed of or containing same.

In the context of the present invention, the term "isolated", as in, for example 'isolated from biological tissues or cells', refers to any process which separates the therapeutic material of interest from the tissue or cell membranes in a manner which preserves the structure and function of therapeutic material of interest. The term "isolated" as used herein is synonymous with the terms "extracted" and "harvested", for example.

In addition to being isolated, harvested or extracted from natural sources, therapeutic materials suitable for use in the instant invention can also be "derived from" biological sources, for example, synthetically produced or produced by genetically engineered plants and animals, including bacteria and other microbes, in accordance with well-known and conventional techniques.

The present invention makes reference to "viscous" materials, particularly as surface coatings for the obstruction of underlying pores. In the context of the present invention, a viscous material is a flowable or pliable material having either a high coefficient of viscosity or a high measured surface tension or both, whereby either or both of viscous forces and surface tension forces serve to retain the material within a pore or interstitial space to thereby obstruct said pore or space and prevent fluid flow therethrough.

The present invention makes reference to the "immobilization" of bioactive agents within an interior core. In the context of the present invention, the term "immobilization" encompasses any number of "capture" and "retention" processes, ranging from ionic or covalent binding to adsorption or absorption to simple physical capture, whether entrapment, entanglement or entrainment. The particular immobilization process is not particularly critical. Rather, what is important is that the process results in a high density of bioactive material being distributed or dispersed throughout the interior core.

B. Illustrative Embodiments of the Present Invention:

As noted above, it is an object of the present invention to provide materials, methods and medical device constructs that enable bioactive materials, and more particularly stem cells, precursor cells and other biological cells, but also including, but not limited to, therapeutic agents such as antimicrobials (also antibiotics, antiseptics, disinfectants and combinations thereof), and bioactive molecules such as growth factors to be delivered to a site of desired therapeutic use, such as for tissue repair or wound healing. Though not intended as limiting to the application, the materials and methods of the present invention enable medical personnel, and more particularly surgical teams, to utilize therapeutic materials that may require immediate use or have restrictive storage requirements, particularly harvested stem cells. Of particular utility are materials extracted from the patient who is the intended recipient of the medical procedure (referred to herein as autografts or autogenic tissues), examples of which include, but are not be limited to, stem, progenitor and other biological cells, bioactive molecules and other therapeutic materials. It is contemplated that the stem, progenitor and other cells and bioactive molecules can be derived from any tissue of the body in which said material is present, including, but not limited to, bone marrow, adipose tissue, muscle tissue and nerve tissue and any fluids associated with those tissues. Alternately or additionally, said cells and molecules can include, in part, materials derived from other sources, including homologous and heterologous transplant material such as allografts, xenografts (also zenografts), synthetic mimics of tissues, or genetically engineered molecules or cells, and that said materials can include bioactive molecules and stem, progenitor and other cells. Alternatively, the cells and molecules of interest in the present invention can be derived from products of the human or mammalian reproductive system, including autografts, allografts and xenografts of the same.

The present invention has particular value in the context of autografts, wherein the bioactive materials of interest are extracted by the surgical team and introduced into the surgical suture or precursor construct, followed by the reintroduction into the patient of the assembled device, preferably all within the context of a single surgical procedure.

As noted above, the exterior sheath and interior core components of a surgical suture, thread-like tissue scaffold or precursor construct of the present invention can take a number of alternate forms. For example, the sheath and core may be fabricated of or from the same or different materials or can comprise a mixture or matrix of materials, wherein elements of the sheath and core are contiguous or otherwise connected. The sheath or core components can exhibit varying degrees of biodegradability or be relatively inert in tissue. They further can be composed of mixtures or matrices of different materials that exhibit different rates of biodegradability in tissue, varying, for example, with the intended application, the target tissue site, and the desired duration of bioactive material deployment.

In one embodiment, the exterior sheath can be constructed of a matrix of a rapidly absorbed material and a structural filament material of reduced absorbability. Such a construction has a number of advantages, all of which, individually or in combination, may be ascribed as goals of the present invention and which further may be extended to other surgical and medical devices, including implants and tissue scaffolds:

1. A less-porous suture sheath or exterior surface which transitions to a more porous state has particular value in the case where biological cells are present in the core. The more porous state can allow molecules necessary for cell growth or survival to permeate into the body of the suture or device where the living cells are, while still retaining the cells in the desired scaffold configuration.

2. The matrix of rapidly absorbed material and structural filament material can present a relatively smooth surface and less-porous surface while the suture is being handled or introduced into the tissue and then the suture surface can transition to a more porous surface once it is present in the tissue. The less-porous surface can present less drag as it is introduced into the tissue. The less-porous surface can also represent an exterior surface that may have a reduced tendency of picking up unwanted molecules or biologics prior to introduction into the tissue. The more porous surface that develops after the suture is present in the tissue can be of value in permitting molecules in the core to diffuse out of the suture for additional therapeutic or antimicrobial value. The rapidly absorbed material can include, at least in part, molecules of antimicrobial or therapeutic value while the structural filament material can maintain the required structural or scaffold properties of the construct.

3. The matrix of rapidly absorbed material and structural filament material can present a relatively smooth surface during the process of passing the suture through the tissue, and then after the rapidly absorbed material begins to dissipate, the suture can exhibit other surface properties such as surface roughness. Increased roughness can be of value in reducing the movement of suture in the tissue, thus reducing the tendency of the suture to "saw" or cut and thus further scar the tissue. Surface roughness can be a factor of: i) increased porosity of the surface, ii) the manner in which the structural fibers are oriented or woven, iii) additional materials or particles which give the structural fibers a rough surface, or iv) other appurtenances or fibers which reorient to protrude from the surface once the rapidly absorbed material begins to dissipate into surrounding tissue.

4. The matrix of rapidly absorbed material and structural filament material can present a surface which does not readily bind to the surrounding tissue during the process of passing the suture through the tissue, and then after the rapidly absorbed material begins to dissipate, structural filament or other material with surface properties which bind to surrounding tissues can be exposed, providing the benefit of fixing the suture in place. The surface properties can include any molecule that can be immobilized on a suture surface with appropriate tissue binding properties, for example, but not limited to, lectins and heparin compounds. A wide range of immobilization techniques for such compounds on polymers are known to those skilled in the art and are of value in the context of the present invention.

The matrix of materials forming the exterior surface, sleeve or sheath of a surgical suture or precursor construct of the present invention typically includes two different synthetic polymers, a synthetic polymer and a natural material or two natural materials, any or all of which may optionally be biodegradable. Such a matrix can be formed by any conventional method known to those skilled in the art of combining materials into a woven, non-woven or film-like construct. Of particular value in the context of the present invention are woven constructs where either:

i) the structural fibers and the more biodegradable fibers are interwoven, ii) the structural fibers and the more biodegradable fibers are woven in two layers with the more biodegradable fibers on the exterior surface, iii) the structural fibers are woven (or laid down as a non-woven structure) and then the biodegradable material is applied as a coating in a manner which fills voids or reduces high spots in the sheath structure, or iv) the structural fibers are woven (or laid down as a non-woven structure) with pliable appurtenances or with short, spike or fur-like fibers protruding from the structural fiber mat and then the biodegradable material (in this case, typically a material that can transition from a moldable form to a more solid or gel form) is applied in a manner which forces said appurtenances or short fibers to lay down on the surface and be held there as the biodegradable material transitions to a more solid or gel form.

The matrix of materials forming the exterior surface, sleeve or sheath of a surgical suture or precursor construct of the present invention can also comprise a porous woven, non-woven or film-type construct which contains within its porous matrix or on either its exterior surface, interior surface or both, an emulsion, suspension, liquid or gel, which exhibits viscous, surface tension or adhesive properties sufficient to be immobilized therein, for a period of time. It is of particular value in the context of the present invention that the period of time be sufficient to permit the assembled device to be implanted in the intended host tissue. Additional time of immobilization may be desired to permit certain biological activities to occur within the confines of the device prior to interaction with the host tissue, such as, but not limited to, replication or differentiation of cells. The embedded or impregnated emulsion, suspension, liquid or gel of the exterior surface can alternatively or further include or incorporate, at least in part, certain molecules having therapeutic value, examples of which include, but are not limited to antimicrobial, analgesic or anti-inflammatory molecules, while an underlying surface contains other molecules or cells with therapeutic value, including, but not limited to bioactive materials such as stem cells. Antimicrobial molecules, at or near the surface, provide immediate functionality to address bacteria or viruses that may be introduced into the patient along with the suture, whereas bioactive molecules retained in an underlying surface may diffuse or be otherwise released over a longer time span, with the intent of having an effect even after any infection has been addressed by the antimicrobials. The present invention contemplates that said emulsion, suspension, liquid or gel can include materials with potential synergistic therapeutic benefits with the bioactive molecules, examples of such liquids including, but not limited to, oleic acid and/or linoleic acid. These molecules are known for anti-microbial properties and thought to have benefits in concert with bioactive peptides such as bone morphogenic protein.

A particularly preferred embodiment of surgical suture of the present invention includes an exterior sheath (or sleeve) of woven or non-woven, including film, fibrous or porous, material and an interior core containing biological cells and/or biologically active molecules (collectively referred to herein as "bioactive materials") and optionally a monofilament or multifilament polymeric material, or combinations thereof. The exterior sheath may optionally be porous and/or, in a further preferred configuration, be provided, at least in part, with a hydrophobic material that affords advantages of reduced wicking, both of polar liquids in the core to the outside of the suture as well as fluids of the host tissue along the suture. The present invention further contemplates a porous sheath having a hydrophobic (also non-polar or less polar) liquid or gel introduced into its pores. This material can (a) serve as barrier for premature migration of cells and therapeutic material from the core of the suture to the exterior of the suture; (b) reduce the infiltration of unwanted material into the suture core during handling; and (c) reduce the friction of a porous suture as it is drawn through tissue and otherwise improve the handling characteristics of the suture.

In a preferred embodiment, a surgical suture of the present invention includes an exterior sheath constructed of interwoven fibers disposed over an interior core of independent fibers or materials. However, the present invention also contemplates an exterior sheath and interior core comprised of a single woven construct, wherein a single fiber can comprise sheath in one portion of its length and core in another, and that in such a construct, the differentiation between sheath and core is that the core retains stem cells and other therapeutic materials in the voids between fibers, and the sheath includes a barrier material, usually a hydrophobic liquid or gel, but also potentially a biodegradable solid, viscous film or material having sufficiently high surface tension.

The present invention further contemplates a surgical suture construct wherein the exterior sheath material is bound to the interior core material or to itself in a manner that constrains movement of the interior core relative to the exterior sheath along their longitudinal axes. This binding can be effected by any number of techniques known to those skilled in the art, including but not limited to, mechanical entanglement across the radius of the suture, thermal or chemical bonding of materials of the suture, or introduction of a bonding material such as a staple.

The present invention further contemplates an exterior sheath in the form of a hollow tube-like structure having inside and outside diameters, the sheath being configured with constrictions at intervals along its length, such constrictions reducing the inside diameter to a point where it reduces or precludes longitudinal migration or movement of material retained the interior core of the suture. Such constrictions can be formed before or after initial formation of the surgical suture or sheath construct; in a preferred embodiment, the constrictions are introduced after the bioactive material of interest is introduced into the interior core. Constrictions can be formed by any number of methods known to those skilled in the art, including but not limited to mechanical deformation such as crushing or twisting, thermal modification such as melting, or introduction in the core of material in addition to the bioactive materials, where the additional material forms a blockage under some external stimulus. The mechanical device that imparts a crushing or twisting action on a specific point in the suture construct can also impart a mechanical pulling force on the suture itself, thereby providing the force necessary to allow assembly of the suture.

In one preferred embodiment of the present invention, wherein the exterior sheath provides at least a partial flow barrier as well as protective benefits and is able to restrain core contents in a linear and confined form, the present invention contemplates the fabrication of the interior core from materials which otherwise would not provide sufficient immobilization of cells and therapeutics for practical use in a suture. For example, multifilament cores can be used to entangle cells and therapeutics due to tortuous flow paths around the filaments, films can be rolled or bunched to provide similar tortuous paths, and/or viscous liquids, foams, gels and emulsions can be utilized. The present invention further contemplates combinations of such materials and processes. Of particular value is the incorporation of an additional material having known benefit to the biological functions or retention of bioactive materials (e.g., stem or other precursor cells) retained in the interior core.

In one embodiment, biodegradable particles containing cells, bioactive molecules and other materials of therapeutic value form the interior core of the suture while a woven structure of suture filaments forms the exterior sheath. The biodegradable particles can include polymer or natural constructs with embedded or surface expressed bioactive molecules, antimicrobial molecules or other molecules of therapeutic interest. The particles can be of any size and geometric configuration which is conducive to introduction of said particles into the suture core and which permits a majority of particles to be retained in the core during the process of introduction of the suture into the target tissue. The particles can have stem or other biological cells adhered to their surfaces or in a matrix, or they can have moieties that bind to the same.

The present invention also contemplates the use of nanowires (also nanofibers and microfibers) as binding or entanglement constructs in the core of a suture, or as flow impeding constructs in a porous sheath. Further, such nanowires can exhibit a degree of entanglement in a multifilament suture structure, with inherent benefits in retention of bound or embedded materials. Additionally, nanowires can be induced to form hydrogels, and the inclusion of hydrogels in the core of the suture is also a valuable aspect of the present invention.

The present invention also contemplates bioactive molecule binding moieties as described by Stupp et. al. in US Patent Application 2005/0209145, introducing those moieties into tissues and their derivatives extracted from a prospective patient, or allografts or xenografts of the same, optionally concentrating the tissue solution before or after addition of the moieties, allowing conjugation of bioactive molecules present in the tissue with the binding moieties taught by Stupp, allowing the nanowires to form and mechanically embedding the nanowires and optionally biological cells from the tissue solution in the matrix of a multifilament suture. As such, nanowires provide benefits in immobilization and delayed release of the bioactive materials that are beneficial in tissue growth and can be utilized in conjunction with stem cells to good effect.

The present invention further contemplates affording the exterior sheath and/or interior core of a surgical suture of the present invention with one or more surface molecules or films that represent potential binding or bonding sites for cells or therapeutic molecules. The binding or bonding may arise through chemical conjugation, absorption and/or hydrophobic interaction or other mechanisms for bonding cells or molecules to substrate materials that are known to those skilled in the art. Of particular value in the current invention is the propensity of stem cells to bind to certain materials, most notably polymers (also plastics). Heparin, heparin derivatives and heparin bearing compositions are also of particular value in the context of the present to create appropriate binding surfaces in suture sheaths and cores.

Protein-coated polymer core fibers are also specifically contemplated in the present invention due to the propensity to promote the binding and growth of cells. Christopherson, et al. of Johns Hopkins University have demonstrated the value of laminin-coated electrospun Polyethersulfone (PES) in fiber meshes for adherence and growth of stem cells.[6]

[6] Christopherson G T, et al. "The influence of fiber diameter of electrospun substrates on neural stem cell differentiation and proliferation". Biomaterials, 30 (4): 556-564 (2009).

To facilitate introduction of potentially perishable biological material, particularly stem cells or allogenic materials, or expensive therapeutics into the present invention, the present invention contemplates the provision of kits composed of i) a sterile package, or one that can be sterilized, ii) one or more sutures or other medical devices contained within the sterile package; iii) provisions for stem cells, other biological cells or therapeutic materials to be introduced into the interior core of a suture or precursor construct thereof prior to introduction of the assembled suture into the intended host tissue and iv) provisions which will encourage retention of the cells or therapeutics within the interior core during the process of introducing the suture into the intended host tissue.

In one preferred embodiment, the provisions encouraging retention of the cells or therapeutics within the interior core during the process of introducing the assembled suture into the intended host tissue involve the introduction of bioactive material such as cells and therapeutics into the interior core through passages that are then further restricted to inhibit seepage. In one aspect, the bioactive material is introduced through the pores of the exterior sheath, and then another material that acts as a barrier is introduced over the sheath and into its pores. In another aspect, the dimensions of the pores in the exterior sheath are manipulated, for example through compression, extension or other mode of deformation, after the bioactive material is introduced, typically by elongating the sheath along its longitudinal axis in a manner which increases the length but reduces the width of the pores to a point where the reduced width serves as a limiting dimension for material flow across the exterior sheath. In another preferred embodiment, the bioactive material is introduced into the interior core either prior to introduction of the interior core into the exterior sheath or through an end of the exterior sheath. Additional details on this embodiment are presented below.

As noted above, the kit can include provisions (e.g., ports) for introduction into the sterile package of bioactive materials or antimicrobial materials or protective or otherwise useful materials, including, but not limited to flushing agents, binding agents or coating agents, and that these provisions find particular value when configured to permit medical personnel to introduce into the package materials extracted from a prospective recipient which are thought to include stem cells or other biological cells or therapeutic molecules. Such provisions for the introduction of target agents can include, but are not limited to, areas for injection of, or otherwise introduction of, fluids or other materials into the sterile package where the package is then resealable or self-sealing, as might be envisioned by those skilled in the art. Further the kit can include provisions for removal from the package of excess target agent(s), and that these provisions (also ports) can include, but need not be limited to, areas for extraction using hypodermic needles, one-way valves, deformable polymers which separate and allow flow out when sufficient pressure is exerted on the package, or other directional flow limiting, reseal-able or self-sealing devices as may be envisioned by one skilled in the art. A properly designed port, can in certain aspects of the present invention serve as both a port for introduction of material as well as a port for removal of material. In other cases, there may be advantages to a package having a proximal end and a distal end, such that the introduction port is located at the proximal end of the package and the discharge port is located at the distal end of the package. A dual port package provides the advantages of a flow through design that ensures that the target agent(s) is well distributed in the package and consequently has an increased probability of contact with all relevant portions of the suture or device.

The present invention also contemplates a kit which may be configured to permit one or more target agents, including, but not limited to, stem cells, other biological cells and therapeutic molecules, to be applied to a portion of the surgical suture or precursor construct and then permit in a subsequent step the coating or otherwise covering of this same portion with an additional target agent or agent(s), examples of such second agent(s), including, but not limited to antimicrobial molecules and/or hydrophobic coating molecules, for example fatty acids, or other therapeutic or protective coatings, in a manner where upon removal of said device from the package, the assembled surgical suture exhibits certain surface properties of protective or therapeutic use associated with the second agent(s) while the interior of the device exhibits additional or other properties of therapeutic use related to the first agents(s). As an aspect of the present invention, the kit can include any configuration for sequential application of material, including, but not limited to i) sequential introduction of material in one package zone, and ii) passage of said device through two or more package zones where different materials can be applied prior to or during removal of the device from the package. In the case of a package with two or more zones for application of target agents, in certain aspects of the present invention, each zone may have agent introduction or removal ports.

In the context of the present invention, a medical device, such as a surgical suture or elongate tissue scaffold may, but is not required to be, contained in the package in a manner wherein the suture is not exposed to a particular package zone where a target agent is present until one end of the suture is drawn from the package, an action that then initiates movement of the suture material into and through the zone with the target agent.

As noted above, the exterior sheath of the surgical suture or precursor construct may include a non-polar liquid embedded within the woven or non-woven matrix of a multi-filament material or a porous film. This non-polar liquid can provide several valuable properties, including i) lubrication when the device is a suture material and the suture material must pass through tissue with a minimum of friction, ii) synergistic benefits when acting in concert with bioactive molecules, such as with the potential synergy between various growth factors and oleic acid, and iii) through surface tension an additional barrier to the premature leakage of materials within the sheet to the exterior.

As noted above, the present invention contemplates a method of applying a target agent to a portion of a suture or medical device and subsequently coating or covering that portion with other agents or materials, the method including the following steps:
  i) providing a prepared medical device, such as a pre-assembled surgical suture, in a sterile package having a port for allowing sterile passage of at least one target agent to the device;
  ii) optionally introducing a binding agent to facilitate binding of a target agent to the medical device and optionally inducing excess binding agent to be expelled from the package through a port;
  iii) introducing a target agent into the package through a port to interact with the prepared medical device;
  iv) inducing a portion of the target agent which fails to bind to the medical device to be expelled from the package through a port;
  v) optionally introducing a flushing material into the package to assist in diluting and removing excess target agent and subsequently inducing the flushing material to be expelled from the package through a port;
  vi) introducing an additional target agent, agents or coating molecules into the package through a port or otherwise cause an additional target agent, agents or coating molecules to be released in the package in a manner which results in the agents or molecules coating the medical device.

Alternatively, the present invention contemplates a method of applying a target agent to a portion of a suture or medical device in one zone of a package and then moving that portion to another zone of the package wherein that same portion is exposed to additional agents or materials, the method including the following steps:
  i) providing a prepared medical device in a sterile package having a port for allowing sterile passage of at least one target agent to the device;
  ii) introducing a target agent into the package through a port to interact with the prepared medical device;
  iv) inducing the agent exposed portion of said device to move to another zone of said package, wherein the device is exposed to an additional agent(s) or coating molecule(s).

In the context of the present invention, suitable packages for applying of multiple target agents to a surgical suture or medical device can include:
  i) a container or reservoir for receiving the device;
  ii) a port in communication with the container or reservoir for allowing sterile passage of a least one target agent, referred to as a first agent(s), to the prepared device;
  iii) a second container or reservoir containing an additional target agent or agents (including, but not limited to antimicrobial molecules and hydrophobic coating molecules), wherein the second container can be induced by external stimulus to release the additional target agents into contact with the medical device, thus permit a medical device which has been exposed to a first agent(s) to be subsequently exposed to or coated by a second agent(s).

In a preferred embodiment, the additional, final agent expressed on the surface of the device as it is removed from the package comprises a hydrophobic liquid having lubricating and sealing properties, particularly a fatty acid, and/or an antimicrobial material.

As noted above, the assembled suture or tissue scaffold device of the present invention can take the form of a monofilament or multifilament material, such filaments including those of approximately cylindrical geometries, as in common use, as well as other cross-sectional geometries, including, but not limited to, film or tape-like geometries. Additionally, the packaged kit can include suture material in any configuration that allows for the dispensing of the suture material in a sequential manner without tangling as can be envisioned by one skilled in the art. Such dispensing systems may be analogous to those presently available in the art for dispensing suture material, string, wire, dental floss and tape, thread and similar material. In the context of the present invention, the package may contain a length of suture material suitable for use in a single patient, or on a single wound. Alternatively, the package may contain suture material in multiple discrete lengths or a continuous length that can be separated into discrete lengths.

The present invention contemplates the inclusion of one or more surgical suture needle or analogous devices in the packaged kit for use in conjunction with the suture material. The needle facilitates the penetration of tissue and pulling of the suture material through the tissue, and, as such, may be integrally with or attached to the suture material while in the package to alleviate any need for threading the suture material into a needle or otherwise attaching it thereto. In the context of the inventive kit, the sharp tip of the needle may be afforded with a point protector, for example a piece of material that the point cannot easily puncture. Alternatively, the needle can be mounted in the package in a manner that reduces the potential of puncture wounds during handling or opening of the package.

Kits and packages of the present invention may include an area within or outside of the sterile package where materials extracted from a prospective patient, for example those presumed to include stem cells, other biological cells of interest and/or molecules of therapeutic value (bioactive materials), can be introduced as part of a liquid solution (also bioactive solution), the package design being such that the suture material is in physical contact with this solution while in the package or as it is extracted from the package for use, as is readily envisioned by one skilled in the art. The present invention further contemplates that the area of contact between said bioactive solution and the suture material can take the form of a separate or isolated zone, preferably sterile, within the package which is designed to accept introduction of the solution through a hypodermic needle or analogous dispensing device into a zone which is configured to maximize the contact between solution and suture material while in the package or as the suture material is extracted from the package. Such a configuration may take the form of an expandable area containing the suture material, such that the suture material is in immediate contact with the solution when the solution is introduced into the package. Such a configuration could also involve a tube-like or other geometry section which holds the introduced solution and which the suture must pass through as it is drawn from the package, the intent being to minimize the potential of bioactive molecule containing fluid sitting in unproductive pockets which are not disturbed by the passing of the suture material through said area of the package. More complex mechanisms can also be envisioned for contacting bioactive molecule containing fluid with the suture material by those skilled in the art.

The present invention contemplates that the surgical suture or precursor construct contained within the sterile package can include a leader section of suture material. The leader section is a length of suture material which is not intended to include bioactive materials but is contiguous with the remainder of the suture material which does include bioactive materials. The leader section may extend from a zone where suture material and bioactive molecule solution are in contact to an area outside that zone, wherein the leader section can be accessed to be grasped, by hand or tool, and pulled to extract the bioactive molecule coated section of the suture from said contacting zone. Further, the leader section can optionally be treated in a manner which provides for more effective termination of the suture in a wound repair, such as with material which exhibits improved knot holding characteristics, and that a tail (or distal) end of the suture can exist on the opposite side of the bioactive materials zone of the suture, where said tail end possesses similar properties as the leader section. The leader portion, and optionally tail portion, of the suture material can be differentiated by means of (a) a visual identifier such as a difference in color, shade, texture and pattern, and/or (b) a difference in one or more physical properties such as concentration of bioactive material, knot holding characteristics and handling characteristics. Accordingly, the suture material can be positioned in the package such that the suture material forms a continuous chain from the zone where the bulk of the suture material is stored, for example, through the zone where the bioactive material can be added, which may or may not be the same zone where the bulk of the suture material is stored, into the leader zone of the package where optionally a needle or other such device may be packaged, and where the package may be conveniently opened by the user at the time of use. Consequently, the package will typically be opened by some means of access to the leader zone and said access can be as simple as cutting or tearing open the packaging at the leader zone to expose the suture leader material or surgical needle.

The leader material may take the form of a monofilament, multi-filament or film-type construction and of any material of adequate tensile strength to allow it to be extracted from the surrounding sheath by tension placed on the leader material in opposition to tension placed on the sheath material. Further, the distal end of the leader material is preferably joined in a contiguous manner with the proximal end of a section of monofilament or multi-filament material suitable for service as the interior core of a surgical suture. As noted above, the leader material can be color coded or otherwise delineated to indicate the point where drawing of the leader out of the sheath can be stopped to present optimum positioning of the interior core within exterior sheath.

Also contemplated is a surgical suture in which the distal end includes a section of material having a larger cross-sectional area than the cross-sectional area of any other point along the length of the suture construct, henceforth referred to as a distal-stop. A suture of this configuration may also, but is not required to have a suture needle attached to the proximal end. As noted above, the distal-stop can be fabricated of any variety of materials and in a variety of configurations. For example, the distal-stop can be of the same material as any part of the suture, or it can be of a different material joined to the suture. When a suture with a distal-stop is pulled through the tissue of a patient, the distal stop can serve to stop and otherwise anchor the end of the suture at surface of the tissue due to the enlarged size and thus alleviate any need for tying a knot or otherwise anchoring the suture at that point. The distal-stop can also include surface features or holes that allow the suture to pass through the tissue and then be stitched back through the distal-stop, providing a force distribution plate for the suture stitch. The distal-stop can also include one or more of the following features: (i) be of a biocompatible nature; (ii) be of a biodegradable nature; (iii) include therapeutic materials, including but not limited to growth factors; (iv) be a design which distributes the force from the suture on the surrounding tissue; (v) include any geometric configuration which may also facilitate the use of said attached material as a suture anchor in tissue or a prosthetic device; said geometric configurations can include, but are not limited to holes or loops where suture material could be passed through, configurations which permit use as an anchor plug in a hole through bone, cartilage or synthetic devices, screw threads, expansion type anchors, configurations compatible with screws, pins, staples and other implant devices and other configurations as might be envisioned by those skilled in the art.

A surgical suture, more particularly an exterior sheath or sleeve thereof, may be hydraulically connected or otherwise mechanically anchored at its distal end to the interior of dispensing syringe (also hypodermic) needle, tube or other analogous device which is, in turn, attached to a reservoir which may contain bioactive material or, in the kit of the present invention described earlier, is connected to the package zone where bioactive materials are introduced. In the simplest form, bioactive materials can be injected into longitudinal voids in the interior core of the suture or the hollow exterior sheath to form an assembled surgical suture construct.

The present invention further contemplates the positioning of the interior core such that it extends through the distal end of the dispensing tube and concentrically through the zone of the dispensing tube which contains the exterior sheath on the exterior and further that at, or at a point removed from, the proximal end of the dispensing tube, the exterior sheath and interior core are positioned or joined in a manner where the two can be drawn upon as a single entity. The present invention further contemplates a method wherein exterior sheath and interior core at the proximal end of the dispensing tube are pulled in a direction away from said tube such that fluid in the tube can be dispensed into the zone between interior core and exterior sheath and, in this motion, the sheath is drawn off of the outside of the dispensing tube at the same time that the interior core containing bioactive material is drawn out of the interior of the tube, thus forming an assembled suture construct of exterior sheath and interior core at the proximal end of the dispensing tube. The fluid in the reservoir can be imparted with a force to promote flow through the dispensing tube and into the interior core and sheath which forms during this process. Optionally, the suture construct can be drawn into a tube of appropriate diameter to concentrically contain the suture construct as it forms, and that said tube can be of any material which either provides a guiding scaffold for suture construct formation, or a protective sleeve to avoid suture damage or contamination, or an additional means of providing exterior material of value on the suture construct. The intermediate and final constructs of the above method are further aspects of the present invention.

The proximal end of an interior core material is preferably positioned at the distal end of an exterior sleeve sheath and extends into the dispensing syringe needle, tube or other device, or kit package, such that when a leader section is extracted from the proximal end of the exterior sheath, it draws the interior core through the distal end of the sheath and into the sheath, and further that such action results in biological cells and bioactive material, contained in the reservoir, being introduced into the interior core of the suture sheath. The cells and bioactive material may be drawn into the area between the interior core and exterior sheath through friction forces, and/or the interior core material may contain, embedded, adsorbed, absorbed or conjugated onto the core material, cells and bioactive materials as may be contained in said reservoir or applied to the core material prior to placement in said reservoir. The sheath or core material may also have embedded in the matrix of its construct any material which may provide benefits of reduced friction between components, increased retention of cells and bioactive material or anti-microbial properties. Examples of such embedded material include, but are not limited to, natural materials such as fats and oils, synthetic materials such as silicones and polymers, known suture lubricants, and combinations thereof.

The present invention contemplates imparting force onto the fluid in the package reservoir to promote movement of bioactive material into the interior core. In the context of the present invention, a variety of forces can be used to impart movement of fluid and bioactive materials into or onto the suture matrix, these forces can include, but not be limited to, pressure or compressive force, gravity, centrifugal force, friction or other mechanical forces, electrical force, osmotic forces and any other force which one skilled in the art might employ.

The present invention contemplates incorporation in the interior core of discontinuities, voids or patterns as might be readily envisioned by those skilled in the art to facilitate the inclusion of cells and bioactive materials in the zone between the exterior sheath and the interior core or within the interior core during the process of drawing of the core into the sheath. Examples of such patterns can include configurations designed to restrict flow of cells and bioactive materials along the length of the core material once the sheath and suture core are in their final assembled orientation, for example, periodic sections of core material of a diameter which is equal to the inside diameter of the sheath, effectively forming a hydraulic or material flow barrier. As noted previously, the interior core can be fabricated of multiple filaments, or of one or more tape-like films, which prior to being drawn into the suture sheath are presented in a splayed configuration that maximizes the surface area in contact with the bioactive material, the interior core material then gathered into a more dense configuration as necessary to fit inside the exterior sheath. In fact, the gathering process itself can result in entrapment of cells and bioactive material, with the gathering being the result of a random compression of the interior core or a more ordered alignment as might be achieved through twisting or other action on the core material.

The present invention contemplates the concentric containment of the exterior sheath within a tube or other package to prevent contamination prior to use, such tube or protective package being suitable to undergo sterilization prior to handling and capable of being removed immediately prior to or during insertion of the suture material into tissue.

In another configuration, the exterior sheath may be concentrically positioned on the outside of a dispensing tube, as described above, and held in compressed state along its longitudinal axis with the result of a shorter length and greater diameter. This can be achieved either through forming the sheath in a state where it can be subsequently extended along the longitudinal axis, or alternately, through forming the sheath and then compressing it along the longitudinal axis. When such constructs are extended along the longitudinal axis, the construct contracts around the axis; the diameter decreases. In the case of a woven construct, the movement in some cases creates a tighter weave. When the same device is compressed along the longitudinal axis; the diameter increases. Of particular value in the context of the present invention is a suture sheath which can be stretched from a compressed state to an extended state along the longitudinal axis by a ratio greater than or equal to 2:1; for example, a suture sheath which is 10 cm long in a compressed state is 20 cm long in an extended state.

The present invention also contemplates a method whereby a multifilament suture material that is woven in a manner which forms an extensible exterior sheath as described above is compressed along its longitudinal axis and the diameter increased sufficiently, so that a dispensing tube, such as a hypodermic needle or other hollow material dispensing device or surrogate, is inserted along the axis through the core of the suture material woven sheath; alternatively and preferably the suture material sheath is woven directly on the exterior of said dispensing tube, or appropriate proxy for later transfer onto a hollow material-dispensing device; at the appropriate time, a syringe or other fluid reservoir is attached to the hypodermic needle and loaded with bioactive molecules; the contents of the dispensing device are then discharged into and out of the dispensing tube while the woven suture material sheath is drawn off of the dispensing tube in a manner where the woven sheath increases in length and decreases in diameter at the discharge point of the needle, effectively trapping and compressing the bioactive material and other substances in the core of the suture. The suture construct can then be drawn into a second tube of appropriate diameter to concentrically contain the suture construct as it forms, and that said tube can be of any material which either provides a guiding scaffold for suture construct formation, a protective sleeve to avoid suture damage or contamination, or an additional means of providing exterior material of value on the suture construct.

The present invention further contemplates an assembly comprised of a suture needle, with a proximal end (also leading or point end) and a distal end (also trailing end, attachment end and in some cases swage end), and a suture having both exterior sheath and interior core, such that the proximal ends of the suture sheath and the suture core are concentrically joined and attached to the distal end of the suture needle using attachment configurations known to those skilled in the art of surgical sutures; wherein the suture sheath and suture core are of similar length when extended under tension along the longitudinal axis, and wherein the suture sheath is compressed along the longitudinal axis towards the proximal end, or formed in a compressed state, such that the suture core material is presented in a manner where it can be easily exposed to materials with therapeutic value, including stem and other biological cells, bioactive molecules, and other materials. Such an assembly can be part of the kit as described earlier, where the construct is contained in a sterile package, and the suture core material is contained within a package zone where bioactive materials or other materials with therapeutic value can be introduced. Alternatively, the kit can contain a point of restriction, either within or outside the package, such that the diameter allows passage of the suture needle, but requires the suture sheath to extend along the longitudinal axis in order to pass through the restriction, effectively encasing the suture core and embedded therapeutic materials inside the suture sheath along the length of the suture construct.

The present invention further contemplates a suture sheath material which is in a state prior to being extended, also stretched, along the longitudinal axis to form the suture construct, can have a proximal end where the sheath material is attached to either a suture needle, the suture core, or is otherwise anchored to a point which will move away from the distal end in a stretching process, and a distal end, and that the distal end can be of a nature which facilitates implementing relative motion opposite that of the proximal end. The distal end feature can include any mechanical configuration as is readily envisioned by those skilled in the art, including the above-described distal-stop configurations. The sheath distal-stop can have mechanical interference with an area in the suture packaging or bioactive material dispensing apparatus which allows the proximal end of the suture to be drawn away from said packaging or dispensing apparatus which the distal end remains in place, thereby stretching the sheath material over the core material while bioactive material is dispensed into the suture. The sheath distal-stop can also serve the purposes previously disclosed for a suture distal-stop. Additionally, it is the aspect of the present invention that the suture core can also comprise an enlarged area at the distal end of the suture core, a core distal-stop. This core distal-stop can be of any configuration or material and possess properties similar to a suture distal-stop. It is an aspect of the present invention that the core distal-stop can also be of a design to mate up against the sheath distal stop in a manner which prevents the distal end of the core from passes into the distal end of the suture. The core distal-stop can be of a design where it mechanically or otherwise engages with the sheath distal-stop in a manner where further relative movement between the two distal-stops is inhibited; many mechanisms for achieving this can be envisioned by those skilled in the art, the simplest of which is an interference fit where the core distal-stop snaps into place in the center bore of the sheath distal stop. The engagement between the sheath distal-stop and the core distal-stop can result in a partial or complete hydraulic seal that inhibits flow of material from the core out through the distal end of the suture.

As noted above, the present invention contemplates the provision of an interior core in the form of a film or tape-like material. This film, with or without bioactive molecule binding moieties, can be exposed to bioactive material (stem and other biological cells, bioactive molecules, and other material with therapeutic value), and then twisted around the longitudinal axis to form a suture core that mechanically and otherwise entraps the bioactive material in the resulting construct. Such a twisted construct can then be subjected to any number of processes which are apparent to those skilled in the art to bind the construct in the twisted form, such processes include but are not limited to gluing, coating, melting in part or in whole or mechanical stapling or otherwise entangling film layers. Such a film construct can also be formed with cells and bioactive material on one side and binding material on the other, such that twisting or mechanical compression of the film causes self-binding into a suture construct. Such a film construct may include a release paper/film on the binding material side during exposure to cells and bioactive material and prior to formation into a suture.

C. Methods of Making and Using Embodiments of the Present Invention

When bioactive molecules, for example growth factors, are introduced into an area of the body, they can afford a therapeutic benefit to the local tissue only so long as they are present in appropriate concentrations. Without means of immobilizing such bioactive molecules in a target area, the circulatory systems in the body may quickly transport the bioactive molecules out of the area, resulting in only a portion of the intended therapeutic benefit. A wide range of technologies have been proposed for the immobilization of bioactive materials, many of which are useful in the context of the present invention.

The binding of members of the TGF-β cytokine superfamily (growth factors) to heparin and heparin sulphate containing molecules is known.[7] In U.S. Pat. No. 6,921,811, the entire contents of which are included herein by reference, Zomora, et. al., teach the coating of medical devices with a silyl-heparin complex and a bioactive molecule directly bound to the heparin-activity molecule. In the Zomora patent, the silyl-heparin complex adheres to the medical device through hydrophobic bonding interaction. Creation of film coatings containing growth factors as taught by Zomora, can find utility in certain aspects of the novel constructs of the current invention which utilize self-assembled films.

[7] C. C. Rider, "Heparin/heparin sulphate binding in the TGF-b cytokine superfamily", Biochem. Soc. Trans. (Great Britain), 34: 458-460 (2006).

In US Patent Application 2005/0209145, the entire contents of which are included herein by reference, Stupp, et. al., teach the creation of peptide compounds which incorporate the growth factor recognition product of a phage display process and the binding of those compounds to targeted growth factors. Stupp, et. al. also teach the use of these compounds in the creation of self assembled nanofibers or micelles. Certain of the techniques described by Stupp et al. may find utility in connection with the immobilization of bioactive molecules in constructs of the present invention.

Discher, et. al., teach the creation and use of polymersomes and related encapsulating membranes in U.S. Pat. Nos. 6,835,394, 7,217,427 and US Patent Applications 2006/0165810 and 2007/0218123, the entire contents of all of which are included herein by reference. The techniques described by Discher may find utility in connection with the immobilization of bioactive molecules in constructs of the present invention.

Bhaskaran, et. al. in U.S. Pat. Appl. United States Patent 20080058246, the entire contents of which are incorporated herein by reference, teaches methods of synthesizing polymer conjugates of growth factor proteins and other compounds while maintaining a high level of functionality of these biological compounds. These techniques may find utility in the context of the present invention, particularly as a means to immobilize bioactive molecules in constructs of the present invention.

Bioactive glass, ceramics and composites are finding use in medical devices.[8] In particular, silver-doped bioactive glass (AgBG), has been demonstrated as an effective antimicrobial treatment on surgical sutures.[9] This type of material is of value on both internal and external surfaces of the sheath and the external surface of the core material of the present invention.

[8] Boccaccini, Aldo R et al., Expert Review of Medical Devices, 2 (3): 303-317 (May 2005).
[9] Pratten, Jonathan et al., "In Vitro Attachment of *Staphylococcus Epidermidis* to Surgical Sutures with and without Ag-Containing Bioactive Glass Coating", Journal of Biomaterials Applications, 19 (1): 47-57 (2004).

The constructs or methods of conjugating materials can be of value in certain aspects of the present invention, including, but not limited to the bonding of bioactive materials to either the suture sheath or the suture core or in the creation of constructs which can be bound to or imbedded in medical devices of the present invention.

Alkan-Onyuksel, et. al., teach the creation of micelles and crystalline products which incorporate a biologically active compound in U.S. Pat. No. 6,322,810, the entire contents of which is included herein by reference. The methods described in the Alkan-Onyuksel patent may be applicable to certain aspects of the present invention, particularly as a means to immobilize bioactive molecules in constructs of the suture core of the present invention.

The use of HBPA-1 heparin gels (heparin and heparin sulphate) to improve angiogenesis is known and is of value in certain aspects of the present invention. These heparin gels are thought to recruit and activate endogenous growth factors present at a wound site.[10] The use of heparin and heparin sulphate in connection with the suture constructs and longitudinal tissue scaffold devices of the present invention is also an aspect of the present invention.

[10] Corral, Claudio J. MD et al., "Vascular Endothelial Growth Factor Is More Important Than Basic Fibroblastic Growth Factor During Ischemic Wound Healing", Arch Surg., 134:200-205 (1999).

The pre-attachment of a surgical needle (also surgical incision member) to suture material is well-known to those skilled in the art. U.S. Pat. No. 5,226,912, the entire content of which is included herein by reference, is one example of techniques used for attachment. In this patent Kaplan, et. al., teach a construct of a combined surgical needle-spiroid braided suture device. The patent also teaches the concept of inclusion of a medico-surgically useful substance such as a human growth factor in a water-soluble carrier. To be water soluble, a liquid carrier must be polar in nature. This and similar constructs for combining a surgical needle with a suture material may find utility in connection with certain aspects of the present invention.

Multifilament braided sutures are known in the art. In U.S. Pat. No. 5,306,289, the entire contents of which are included herein by reference, Kaplan, et. al., provide an overview of braided suture art and teach the formation of a braided suture having improved properties. Kaplan, et. al., also teach the construct of a braided suture with an increased pick count and a greater number of sheath yarns, wherein said suture also contains at least one medico-surgically useful substance, such as Human Growth Factor.

In U.S. Pat. No. 5,667,528, the entire contents of which are included herein by reference, Colligan teaches a method for attaching a multifilament suture having a sheath and core structure to a surgical incision member. Colligan's method is a use in the context of the current invention wherein he describes techniques for removing a length of core material from the suture to form a coreless sheath. Colligan then uses the coreless sheath as an attachment point to a suture needle.

In U.S. Pat. No. 7,329,271, the entire contents of which are included herein by reference, Koyfman, et. al., teach the construct of high strength sutures woven with absorbable cores. The techniques and constructs described in this patent may find utility in connection with certain embodiments of the present invention.

In US Patent Applications 2007/0170080 and 2008/0128296, the entire contents of both of which are included herein by reference, Stopek, et. al., teach the construct of a medical device package comprising a sealable pouch with a sealed port for introduction of at least one agent to the medical device contained therein. The constructs described by Stopek may find utility in connection with certain aspects of the present invention. Additionally, the present invention provides for improvements on said medical device package systems.

Hereinafter, the present invention is described in more detail by reference to the Examples. However, the following materials, methods and examples only illustrate aspects of the invention and in no way are intended to limit the scope of the present invention. As such, methods and materials similar or equivalent to those described herein can be used in the practice or testing of the present invention.

EXAMPLES

Example 1

A Surgical Suture Kit

Figure 6:
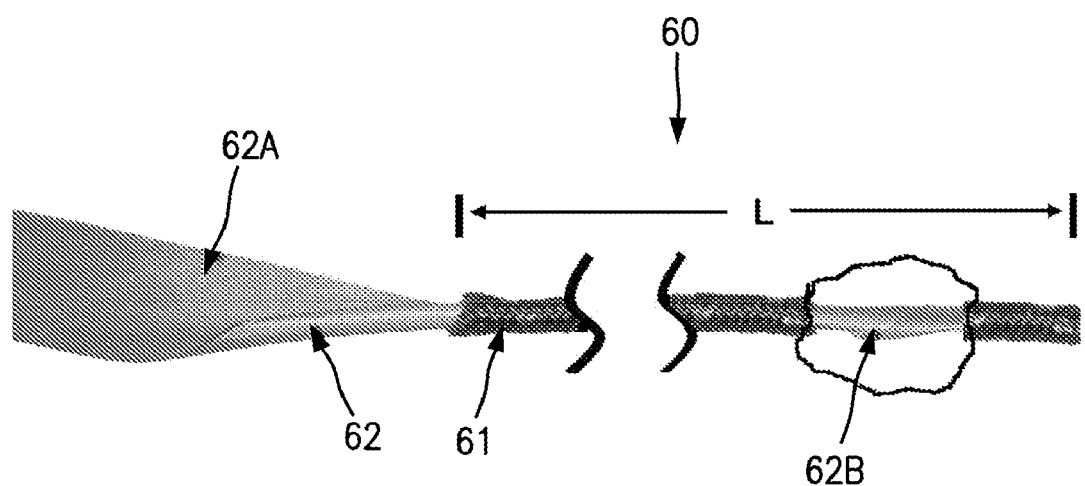
FIG. 6 depicts an alternate example of a precursor construct (60) suitable for use in the fabrication of a surgical suture of the present invention, the construct composed of a film or tape-like core (62) and expansible exterior sheath (61). The film-like core is depicted in transition from an unrolled configuration (left side, 62A), designed for optimum exposure to bioactive material, as it is drawn or gathered into and/or through a length (L) of an exterior sheath (middle portion) to yield a rolled, pleated or crushed configuration contained within the sheath (right side, 62B).
Figure 7A:
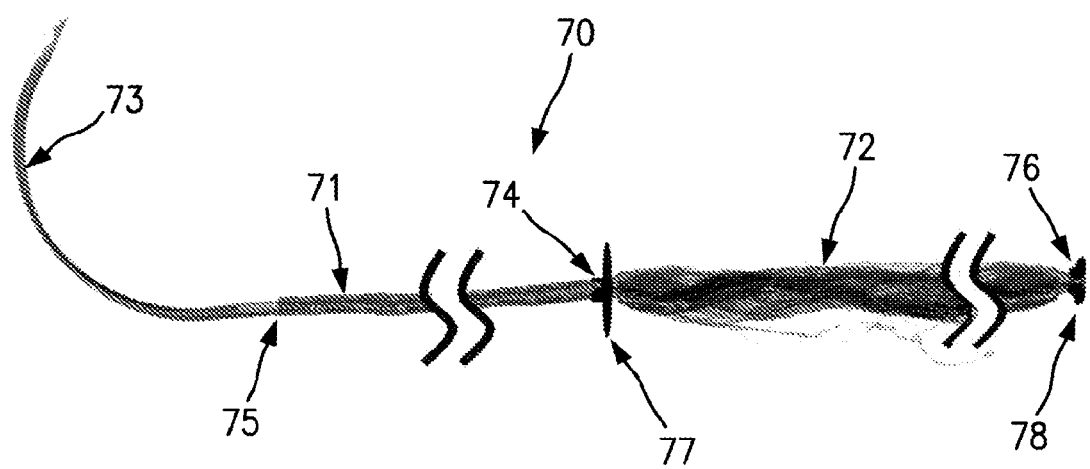
FIG. 7A depicts a pre-assembled suture (70) in conjunction with a conventional suture needle (73), the suture composed of a compressed exterior sheath (71) and a multifilament interior core (72) in an exposed and/or splayed configuration that facilitates the capture of bioactive materials. While sheath proximal end (75) is affixed or otherwise assembled to the suture needled, distal ends of sheath (74) and core (76) are provided with mating stop elements (77, 78).
Figure 7B:
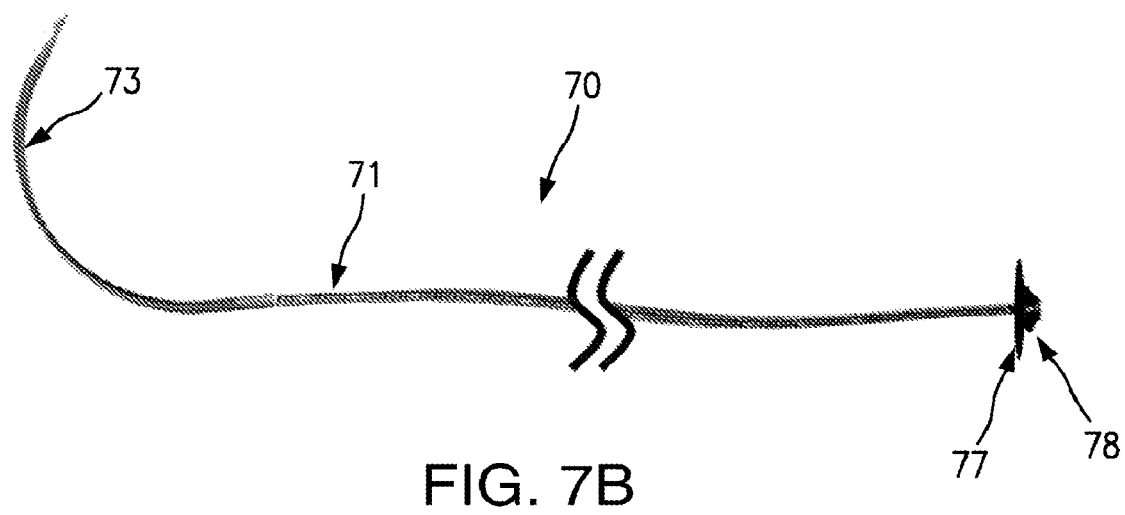
FIG. 7B depicts an assembled suture (70) and needle (73) combination, wherein the exterior sheath (71) has been extended to overlay the multifilament core (not shown), protecting the suture core and the bioactive materials retained therein. In this assembled state, mating stop elements (77, 78) snap or otherwise lockingly engage to prevent relative motion between sheath and core.

As noted above, the present invention contemplates the provision of a surgical suture thread and needle kit contained within a sterile package, illustrative examples of which are depicted in FIGS. 8-11. The suture and needle combination used in connection with the instant example is analogous to that depicted in FIGS. 7A and 7B, being composed of a woven exterior sheath (71) housing a filamentous interior core (72). However, alternate configurations, such as those discussed above and/or depicted in FIGS. 5 and 6, may be adapted as well. In either case, the proximal end (75) of the suture thread (70) is attached to the distal end of a suture needle (73), leaving the sharp needle tip (the proximal end) free for tissue penetration.

Figure 9A:
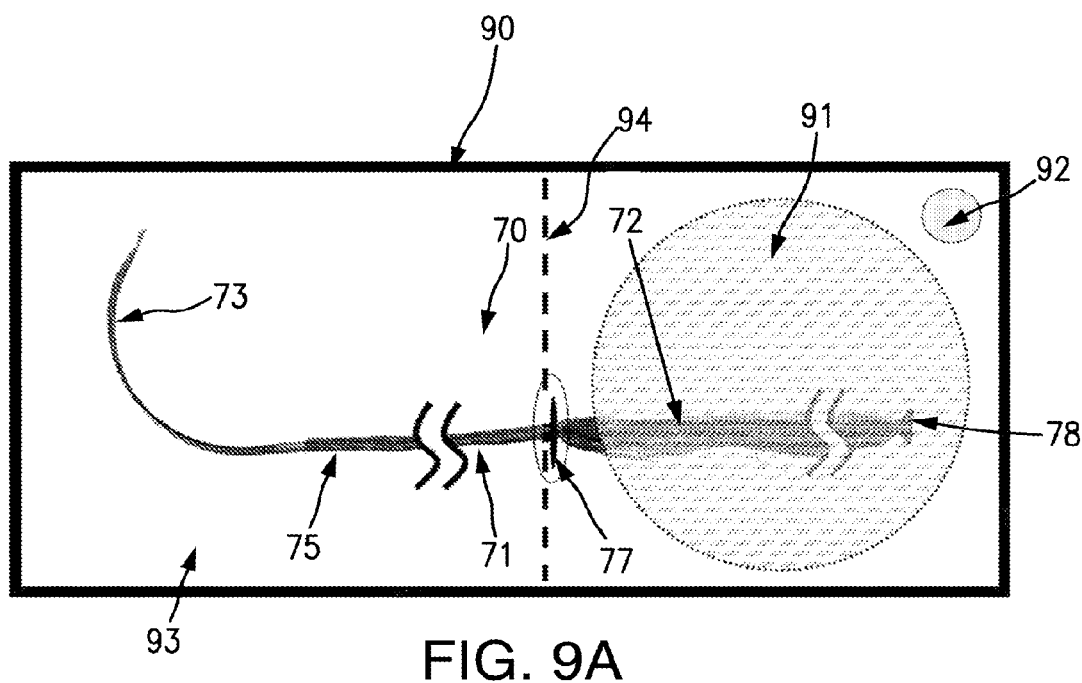
FIG. 9 depicts top down (FIG. 9A) and lateral (FIG. 9B) views of an alternate multi-zoned package system (90) suitable for use in assembling a surgical suture of the present invention from a precursor suture/needle construct such as shown in FIG. 6 or 7. A first zone (91) of the package, taking in the form of an extensible pouch (not shown) or rigid reservoir (shown), houses the exposed multifilament core (72) and distal stop (78) of the pre-assembled suture (70), preferably in a coiled or otherwise unencumbered configuration. This first zone is provided with at least one resealable infusion port (92) for the introduction of bioactive material as well as at least one optional aspiration port for removing excess bioactive material (not shown). A second zone (93) retains the exterior sheath (71) in its compressed state. Also in this second zone, or alternatively external to the package or in an optional third zone, lies the conventional suture needle (73) or like device, the suture needle being affixed or assembled to the proximal end (75) of the suture sheath. First and second zones are separated by a sealing membrane (94) through which the multifilament core may be drawn or pulled. Exterior sheath distal stop (77) is preferably adjacent to the sealing membrane. The sheath distal stop may be pinched between fingers while still in the package and held while the needle is extracted and suture sheath is extended, drawing or pulling the core therein until mating stop elements (77, 78) snap or otherwise lockingly engage to prevent relative motion between sheath and core.
Figure 9B:
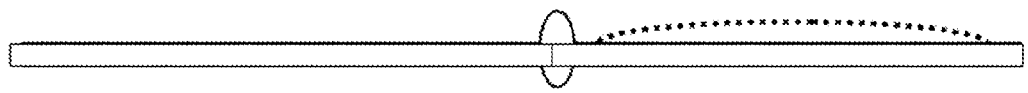
Figure 10:
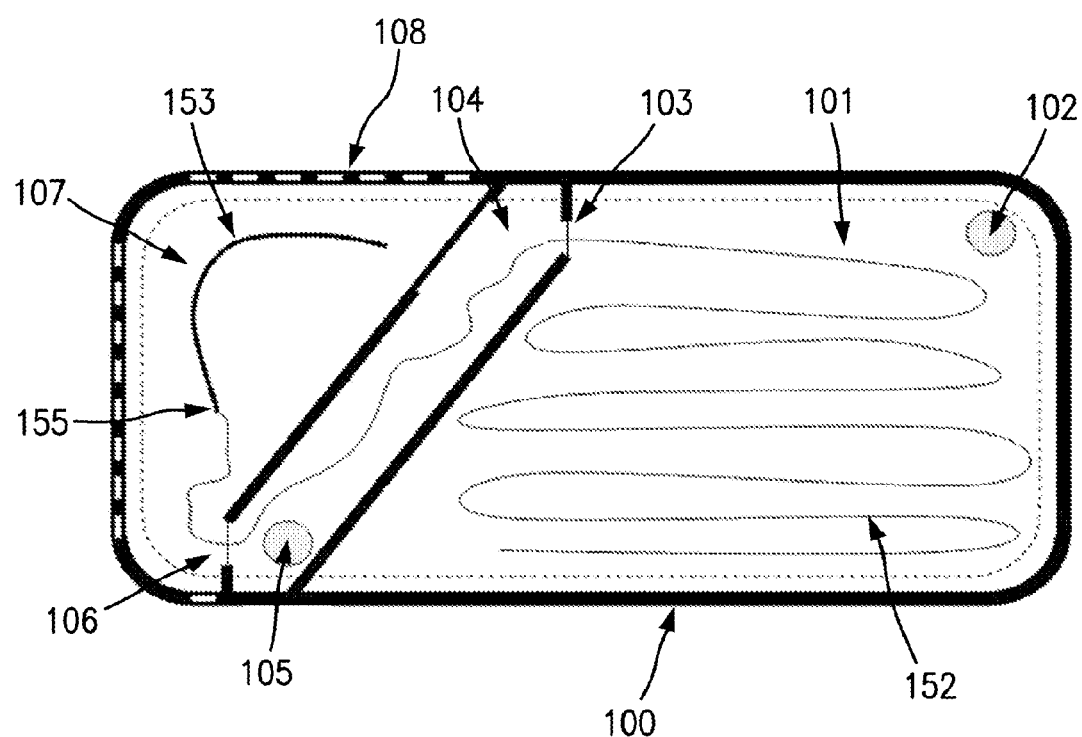
FIG. 10 depicts a top down view of yet another illustrative example of a package system (100) suitable for use in assembling a surgical suture of the present invention from a conventional suture/needle construct. A first package zone (101) preferably takes the form of a reservoir housing the distal end of a suture that is to be imbued with therapeutic material. The suture is deployed in the first zone preferably in a coiled or otherwise unencumbered configuration. This first zone is provided with at least one resealable infusion port (102) for the introduction of bioactive material. Optionally, this zone or other zones may also include an aspiration port for removing excess bioactive material or introducing flushing agents (not shown) or the infusion port may be configured to additionally serve that purpose. A first hydraulic seal (103) separates the first zone from a second zone (104). The second zone is also provided with at least one resealable infusion port (105), for the introduction of additional target agents, particularly sealing agents, to cover the suture surface with additional layer(s) of material in a manner which forms a sheath layer which in the context of the present invention assists in retention of bioactive materials in the core. A second hydraulic seal (106) separates the second zone from a third zone (107) housing a conventional suture needle (153) or like device assembled to a proximal end (155) of the suture. Third zone is optionally provided with one or more frangible seams (108) that facilitate opening of package and removal of the suture needle. In use, the needle is grasped and drawn out of package thereby drawing the suture sheath from second zone to third zone to package exterior, which, in turns draws the interior core from first zone, through second and third zones, and out of package to yield an assembled suture and needle combination (not shown) in which an exterior sheath, comprising one or more coating layers, overlays a bioactive material-containing interior core, thereby protecting the suture core and the bioactive materials retained therein.
Figure 11:
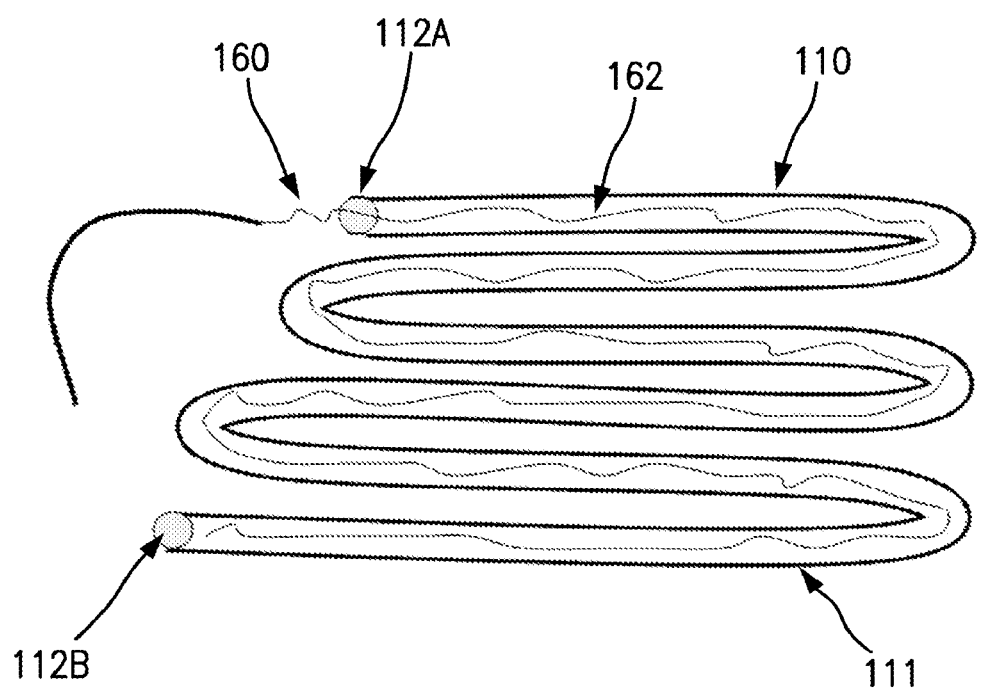
FIG. 11 depicts a top down view of yet another illustrative example of a package system (110) suitable for use in assembling a surgical suture of the present invention from a suture/needle construct (160). The package system depicted includes a package reservoir zone (111) in the form of a tube, though any suitable reservoir shape is contemplated. The package zone houses a distal portion (162) of the suture, preferably in a coiled or otherwise unencumbered configuration. This zone is provided with two or more elastomeric and/or resealable ports, a first port (112A) suitable for the introduction of binding materials, bioactive material, flushing material or sealing material and a second port (112B) suitable for the removal of excess prior to introduction of other material. Arrangement of first and second ports assures a flow-through design in which there are no untreated pockets. The assembly depicted is preferably housed for distribution in a sterile and protective package (not shown).

Referring to FIGS. 7 and 9, the exterior suture sheath (71) is a woven construction of a biodegradable polyhydroxyalkanoate material such as that manufactured by Tepha, Inc. (Lexington, Mass.) while the interior suture core (72) is composed of multiple filaments of polyglycolic acid having heparin compounds adsorbed or otherwise conjugated thereto. When contained in a package system, for example the package system (90) of FIG. 9, the woven sheath (71) is retained in a compressed state in a second zone (93), the exterior sheath being compressed along its longitudinal axis from an extended length of about 30 mm to a compressed length of about 6 mm. The compressed suture sheath material may be saturated with oleic acid, which fills the interstitial spaces of the woven construct and acts both as a lubricant and as a barrier to transport of polar liquids from the interior core to the exterior sheath and vice versa. The distal end of the suture sheath extends through a separating membrane (94) and terminates in a first distal-stop (77), which generally takes the form of a flat washer disk, typically having a 3 mm inside diameter and a 5 mm outside diameter, the disk being 0.5 mm thick along the suture longitudinal axis and constructed of polylactic acid (PLA). The distal end of the suture core is provided with a second PLA core distal-stop (78) that is a dimensional match to the bore of the sheath distal-stop.

Also contained in the package is the interior suture core (72), which extends from a proximal end (76), where it is attached to both needle and suture sheath, through the 6 mm of compressed sheath, through the bore of the sheath distal-stop in a manner where the distal end of the sheath and the sheath distal-stop move freely along the longitudinal axis of the suture core, and into a separate zone (91) of the package, the second zone being at least partially extensible, particularly when a bioactive material of interest (e.g., a slurry or solution of biological cells or therapeutic agents) in introduced into the zone by via a first infusion port (92). In a particularly preferred embodiment, the infusion port takes the form of an area of polymeric or elastomeric material integral with the package wall that serves as a resealable entry point for a conventional hypodermic needle (not shown).

The above-described kit has particular utility in the fabrication of surgical suture or tissue scaffold having bioactive materials isolated from bone marrow incorporated therein. Bone marrow for clinical use is typically obtained as an aspirate extracted from a target patient's bone using a syringe-type device. Often the hip bone is used as a source, due to its large size and proximity to the surface of the body. While some applications permit the use of bone marrow without modification, the present example contemplates the use of a desired fraction (cytokines, precursor cells) that is isolated and separated, using conventional separation technology such as centrifugation.

In the context of the instant example, bone marrow is extracted from the hip of a patient in the course of a routine surgical procedure and the resulting extract is spun down to concentrate bioactive molecules. Cells and molecules from the bone marrow are then injected by syringe through the first infusion port (92) into the suture core zone (91) of the package (90). The needle end of the package is then opened and the needle extracted and pulled in opposition to the package; in this process, the package is held at the point of the sheath distal-stop, such that the needle is drawn away from the suture distal-stop. This motion extends the suture sheath (71), which draws the suture core (72) and biological materials into the center of the sheath. At the full extension, the distal ends of the sheath and core match and the core distal-stop (78) snaps into the sheath distal-stop (77), securing the distal ends together. Once released from the package, the suture is ready for use. In addition to preventing relative movement (and subsequent displacement) between suture core and sheath, the combined distal-stop assembly at the distal end of the suture can serve as a tissue or bone anchor, distributing the force of the suture across an area of tissue or bone, or as a plug in a hole in tissue or bone, or, alternatively, can be configured to coordinate with a prosthetic device. Alternatively, the distal stop assembly can be severed after the suture ends are tied. To facilitate either option, it is preferable that the components be biocompatible; in certain context, it may be desirable for the components to also be biodegradable, and/or comprised of a therapeutic material.

Example 2

Surgical Suture

Figure 5:
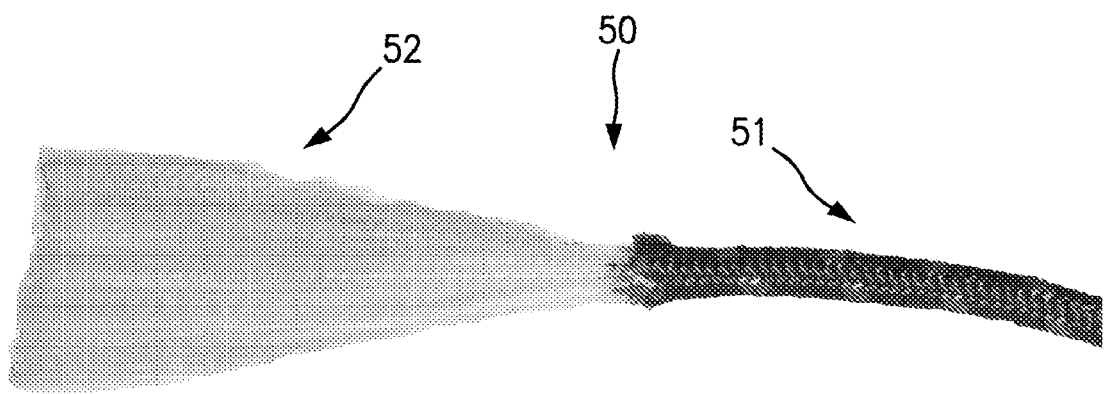
FIG. 5 is a photograph of an illustrative example of a precursor construct (50) suitable for use in the fabrication of a surgical suture of the present invention, the construct composed of a multifilament interior core (52) and an expansible exterior sheath (51). The left side depicts the multifilament core in an initial splayed orientation for optimum exposure to bioactive material; the right side depicts a finished suture construct, in which the sheath is disposed over the multifilament core containing the bioactive material of interest.

The surgical suture of the instant example is analogous to that depicted in FIGS. 5 and 7, being composed of a woven exterior sheath (71) housing a filamentous interior core (72). In particular, the suture was formed with a woven polyester (PET) sheath using 40 denier bundles of 20 filaments each and a pick count of 80 picks/inch, woven over a core comprised of five 220 denier bundles of 100 filaments of UHMW polyethylene (PE). The finished construct was approximately 0.7 mm diameter. The material was cut into 45 cm sutures. The proximal end was connected to a surgical suture needle. The sheath was retracted from the distal end of the suture towards the proximal end of the suture, such that 35 cm of the interior core was exposed. The core fibers were induced to spread through shear motion applied perpendicularly to the linear axis of the core. The construct was then sterilized. The suture core was coated with fibronectin and then exposed to a stem cell bearing fraction of bone marrow aspirate which was obtained using conventional centrifugation techniques. The sheath was then drawn over the core, such that bone marrow components and specifically, the stem cells and other bioactive molecules, were drawn into the core of the suture with the sheath providing both protective and retentive properties on the outside of the construct. The distal end of the suture construct was then knotted to secure the relative position between the distal ends of the sheath and core.

Example 3

Surgical Suture

The surgical suture of the instant example is analogous to that depicted in FIGS. 5 and 7, being composed of a woven exterior sheath (71) housing a filamentous interior core (72). In particular, the suture was formed with a woven polyester (PET) sheath using 40 denier bundles of 20 filaments each and a pick count of 80 picks/inch, woven over a core comprised of a 220 denier bundle of 100 filaments of UHMW polyethylene terephthalate (PE) and a 128 denier bundle of 48 filaments of polyglycolic acid (PGA). The finished construct was in the 0.35 to 0.40 mm diameter range. The material was cut into 40 cm sutures. The proximal end was connected to a surgical suture needle. The sheath was retracted from the distal end of the suture towards the proximal end of the suture, such that 31 cm of the core was exposed. The core fibers were induced to spread through shear motion.

The distal end of the suture sheath was secured to the inside of a package using a biodegradable adhesive. The package was of a design wherein the exposed core was present in a zone where liquids with biological cells and other therapeutic materials can be introduced, similar to that depicted in FIGS. 8 and 9. The package was sealed and the assembly sterilized. A solution containing stem cells was introduced into the interior of the package. The stem cells bound to the PGA filaments of the core. The suture needle attached to the proximal end of the suture was removed from the package and drawn away from the package in a manner which resulted in the sheath being drawn over the core, further entrapping stem cell containing fluid in the core.

Example 4

Surgical Suture

The surgical suture of the instant example is analogous to that depicted in FIGS. 5 and 7, being composed of a woven exterior sheath (71) housing a filamentous interior core (72). In particular, the suture was formed with a woven polyester (PET) sheath using 40 denier bundles of 20 filaments each and a pick count of 80 picks/inch, woven over a core comprised of a 220 denier bundle of 100 filaments of UHMW polyethylene terephthalate (PE) and a 128 denier bundle of 48 filaments of polyglycolic acid (PGA). The finished construct was in the 0.35 to 0.40 mm diameter range. The material was cut into 40 cm sutures.

The distal end of the sheath is attached to the inside circumference of a hollow 3.5 mm×7.5 mm titanium bone screw using a rigid ring of PET which secures inside the distal end of the screw by interference fit. The core of the suture is threaded through the screw and the distal end of the core is attached to a distal-stop of PE which is of a dimension to form an interference fit with the distal end of the bone screw. The sheath and bone screw are then retracted from the distal end of the suture core towards the proximal end of the suture core, such that 31 cm of the core is exposed. The core fibers are induced to spread and are coated with poly-L-lysine. The exposed core section is loosely wound into the inside of a 5 mm diameter×30 mm plastic tube which comprises a frangible hydraulic seal at the bone screw end and a sealable port on the distal end for introduction of biologic material. A surgical team can inject bone marrow aspirate or other biologic containing fluids into the biologics tube at the time of surgery, and then pull the core back into the suture by pulling on the needle end of the suture, thereby trapping the biologics in the suture.

In some instances, the bone screw and attached suture are supplied along with a single use driver as a unit to surgery; the construct of this example can also be supplied in that manner, with a structural extension of the biologics tube, extending over the bone screw and attached driver shaft to create a rigid construct. After the biologics have been introduced, and the core is drawn back through the sheath, screw and driver shaft to a point where the core distal stop engages the distal end of the screw, the biologics tube is removed and the suture is now configured like a conventional suture/anchor/driver set, for use in surgery.

Example 5

Surgical Suture Kit

Figure 8:
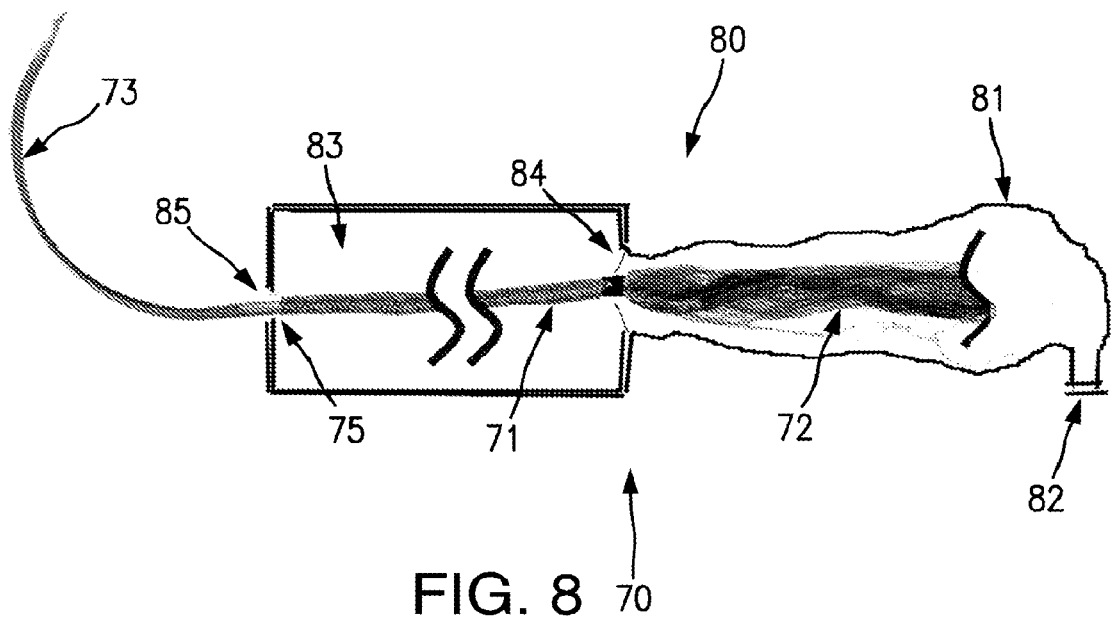
FIG. 8 depicts a top down view of an illustrative example of a multi-zoned package system (80) suitable for use in assembling a surgical suture of the present invention from a precursor suture/needle construct such as shown in FIG. 6 or 7. A first zone (81) of the package, taking in the form of an extensible pouch (shown) or rigid reservoir (not shown), houses the exposed multifilament core (72) of the pre-assembled suture (70) and is provided with at least one elastomeric and/or resealable infusion port (82) for the introduction of bioactive material. A second zone (83) of the package retains the exterior sheath (71) in its compressed state. External to the package or, alternatively, in an optional third zone (not shown), the conventional suture needle (73) or like device is housed, the suture needle being affixed or assembled to the proximal end (75) of the suture sheath. A hydraulic seal (84) disposed between first and second zones impairs leakage of bioactive material out of the first zone. A pinchpoint (85) disposed between suture needle and compressed suture sheath restricts extension of suture sheath until appropriate manipulative pressure is applied.

A surgical suture and needle set is enclosed in a sterile package such as that depicted in FIG. 8 or 9. The proximal end of the needle comprises the point and the distal end of the needle is attached to the proximal end of the suture sheath and the proximal end of the suture core. The suture sheath is a woven construction of polyhydroxyalkanoate. In the package, the sheath is compressed along its longitudinal axis to 6 mm in length from an extended length of 30 mm. The compressed suture sheath material is saturated with oleic acid, which fills the interstitial spaces in the woven construct and acts both as a lubricant and as a barrier for transport of polar liquids from the interior to the exterior of the sheath. At the distal end of the suture sheath, the suture sheath extends through and is attached to a distal-stop consisting of a flat washer disk with a 3 mm inside diameter and a 5 mm outside diameter, the disk is 0.5 mm thick along the suture longitudinal axis and is constructed of polylactic acid (PLA). The suture core is multiple filaments of polyglycolic acid with heparin compounds adsorbed to or otherwise conjugated on the surface. At the distal end of the suture core a PLA core distal-stop is attached which is a dimensional match to the bore of the sheath distal-stop. In the package, the suture core extends from the proximal end where it is attached to both needle and suture sheath, through the 6 mm of compressed sheath, through the bore of the sheath distal-stop in a manner where the distal end of the sheath and the sheath distal-stop move freely along the longitudinal axis of the suture core, and into a separate zone of the package, wherein the packaging is extensible such that therapeutic materials, bioactive materials and biological cells can be introduced by injection through the package wall using a hypodermic needle. An area of polymeric material is provided in the package wall to provide a reseal-able entry point for the hypodermic needle.

During a surgical procedure, bone marrow is extracted from the hip of a patient and spun down to concentrate bioactive molecules. Cells and molecules from the bone marrow are then injected by syringe into the suture core zone of the package. The needle end of the package is then opened and the needle extracted and pulled in opposition to the package; in this process, the package is held at the point of the sheath distal-stop, such that the needle is drawn away from the suture distal-stop. This motion extends the suture sheath, which draws the suture core and biological materials into the center of the sheath. At the full extension, the distal ends of the sheath and core match and the core distal-stop snaps into the sheath distal-stop, securing the distal ends together. The package is then removed and the suture is ready for use. The combined distal-stop assembly at the distal end of the suture can either serve as a surface anchor or stop as the suture is pulled through tissue, or it can be cut off after the suture ends are tied.

Example 6

Multicomponent Sheath

A 0.3 mm diameter suture is constructed of a woven exterior sheath and a linear multifilamentous interior core, such as depicted in FIGS. 5 and 7. The exterior sheath is woven of 80 denier fibers. One quarter of the sheath fibers are fabricated of a copolymer of 50% glycolide and 50% dl-lactide, which degrades rapidly in vivo. The remaining sheath fibers are of polyester material. The interior core is fabricated of UHMW polyethylene filaments which provide tensile strength. The filaments are entrained with self-assembling peptide nanofiber scaffolds with embedded stem cells to yield a stem-cell containing interior core. Once introduced in vivo, the copolymer of the sheath starts to degrade and increases the opportunity for interaction between the interior core and the surrounding environment.

Example 7

Woven Suture

A number 5 suture (a heavy braided suture such as used in orthopaedics, having 0.7 mm diameter and corresponding to 20-21 gauge) is constructed of a 40 denier fiber polyglycolic acid sheath woven such that the fibers are oriented approximately 22 degrees off of the linear axis of the suture. The core also comprises polyglycolic acid fibers. A 30 cm section of suture material is compressed along the linear axis such that the sheath fibers are reoriented to approximately 45 degrees off of the linear axis. The action results in the weave opening up to form interstitial spaces (pores) in excess of 20 microns in diameter in between the fibers. The suture is packaged in this compressed state in a sealed package suitable for introduction of fluids with biological cells and other therapeutic materials. The package includes provisions in the form of a pinch point where the suture must pass through as it is drawn from the package. The pinchpoint puts a linear tensile force on the suture and forces the suture construct to return to the extended state where sheath fibers have a fiber orientation of approximately 22 degrees off of the linear axis, effectively closing off a large percentage of the pore area, squeezing therapeutic materials out of the interstitial spaces (pores) of the sheath and constraining the therapeutic materials in the core of the suture.

Example 8

Stem Cell Immobilization

A number 2 suture (having a diameter of 0.6 to 0.6 mm, corresponding to 23-24 gauge) is constructed of woven sheath of Nylon 6.6, wherein a woven sheath bioabsorbable Polyglactin 910 surrounds a loosely woven core of Nylon 6.6. The sheath is a 20 cm long construct. The core comprises a 45 cm long section which consists of a 25 cm long leader section and a 20 cm long bioactive section. The first 5 cm extends beyond the proximal end of the suture sheath. The next 20 cm is initially positioned within the suture sheath, and the final 20 cm section is positioned within a reservoir for addition of therapeutic materials. The bioactive section of the suture core is surface coated with a film of mineral oil. Bone Morphogenetic Protein-2 (BMP-2) which has been bound to heparin compounds is introduced into the reservoir, such that a film is formed at the interface between the oil and the introduced liquid. The fluid in the reservoir is then replaced with a stem cell bearing fluid. The leader section of core is then drawn out of the proximal end of the suture sheath and as a result, the bioactive section of the core is drawn into the suture sheath along with some of the stem cell bearing liquid and the surface immobilized BMP. The two ends of the sheath are terminated by heat sealing.

Example 9

Electrospun Core

The surgical suture of the instant example is analogous to that depicted in FIGS. 5 and 7, being composed of a woven exterior sheath (71) housing a filamentous interior core (72). In particular, the suture was formed with a woven polyester (PET) sheath using 40 denier bundles of 20 filaments each and a pick count of 80 picks/inch, woven over a core comprised of five 220 denier bundles of 100 filaments of UHMW polyethylene (PE). The finished construct was approximately 0.7 mm diameter. The material was cut into 45 cm sutures. The proximal end was connected to a surgical suture needle. The sheath was retracted from the distal end of the suture towards the proximal end of the suture, such that 35 cm of the core is exposed. The core fibers were induced to spread through shear motion applied perpendicularly to the linear axis of the core. The spread core fibers are positioned in the field of an electrospinning unit producing PLA nanofibers. PLA material equivalent to a mass of less than 0.1% of the total core mass is allowed to accumulate. The resulting exposed core with nanofibers randomly branching between structural fibers is placed in a reservoir containing fibroblasts. The sheath is drawn over the core and in the process the nanofibers and fibroblasts are gathered in to the core.

INDUSTRIAL APPLICABILITY

The present invention provides a means for incorporating a broad range of bioactive materials, such as therapeutic agents, bioactive molecules, and biological cells (e.g., stem cells and other precursor cells), into a medical device construct, such as a surgical suture or thread-like tissue scaffold. Following the principles of the present invention, bioactive material is retained in a defined configuration that permits a gradual release over time and does not necessarily require the chemical conjugation of the incorporated bioactive material to an exterior surface of the construct to effect immobilization, a process known to adversely affect the therapeutic properties of a bioactive molecule.

As a result of the unique design and methods presented, the present invention provides surgical teams with a means to readily, rapidly and routinely utilize bioactive materials, such as biological molecules and cells extracted from a patient, examples of which include, but are not limited to, those present in bone marrow and adipose tissue, in connection with a surgical or medical device which can be then used in the patient. As noted above, endogenous materials have benefits in their composition, being composed of a broad and complex range of bioactive molecules and cells that have been demonstrated to afford therapeutic synergies. Patient-derived materials are particularly preferred, having the distinct advantage of biocompatibility (being native to the intended recipient) as well as the potential to be far less costly than commercially-produced materials and not encumbered by regulatory issues associated with synthetically produced or biologically foreign materials.

The materials and methods presented also provide for increased efficiency of operation in an operating room or other medical procedure environment as well as fewer avenues of potential bacterial contamination of the medical devices in the process of storage, preparation and in-surgery handling. The efficiencies derived from the materials and methods of the present invention can reduce the time in surgery, which, in turn, can reduce the stress on the patient's body and thereby have the potential to reduce the cost of the surgical procedure.

All patents and publications mentioned herein are incorporated by reference in their entirety. Nothing herein is to be construed as an admission that the invention is not entitled to antedate such disclosure by virtue of prior invention.

While the invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

What is claimed:

1. A method of fabricating a surgical suture, the method comprising:
    providing a suture element in an open state, the suture element comprising a plurality of filaments configured in at least one of a braided and a woven configuration to define a plurality of pores or interstices, the plurality of pores or interstices having at least one first size and shape in the open state sufficient to permit a biological cell to traverse the pores or interstices;
    causing a plurality of the biological cells to traverse the plurality of pores or interstices so as to move from an exterior of the suture element to an interior core of the suture element; and
    manipulating the suture element to a closed state, the manipulation of the suture element deforming the plurality of pores or interstices to at least one second size and shape in the closed state, the at least one second size and shape sufficient to restrict migration of the plurality of biological cells from the interior core of the suture element to the exterior of the suture element through the plurality of pores or interstices.

2. The method of claim 1, wherein manipulating the suture element from the open state to the closed state causes a change in a diameter of the suture element.

3. The method of claim 2, wherein the diameter of the suture element decreases.

4. The method of claim 3, wherein decreasing the diameter of the suture element increases a length of the suture element.

5. The method of claim 1, wherein plurality of filaments comprise a rapidly absorbable filament and a structural filament of reduced absorbability.

6. A method of loading biological cells in a surgical suture comprising:
    providing a surgical suture of porous, braided or woven structure characterized by pores or interstices in an exterior surface of the surgical suture, which permit flow of biological cells into an interior of the surgical suture in a first state;
    inducing a biological cell containing media to migrate into the interior of said suture; and
    inducing the pores or interstices in the exterior surface of the surgical suture to a second state where migration of biological cells is inhibited.

7. The method of claim 6, wherein the step of inducing said pores or interstices to a second state includes addition of a biodegradable material into the pores or interstices of the external surface of said suture.

8. The method of claim 6, wherein the step of inducing said pores or interstices to a second state includes deforming the size or shape of said pores or interstices such that at least one dimension of said pores or interstices is reduced and the migration of biological cells is inhibited.

9. The method of claim 6, wherein the wherein the step of inducing said pores or interstices to a second state includes increasing the length of a section of the suture.

10. A method of loading biological cells in a surgical suture comprising:
    providing a surgical suture of porous, braided or woven structure characterized by pores or interstices which permit flow of biological cells into the interior core of said suture;
    inducing a biological cell containing media to migrate into the pores or interstices of the interior core; and
    manipulating the surgical suture by applying force along or around a longitudinal axis of the surgical suture such that the diameter of the surgical suture decreases.

* * * * *